(12) United States Patent
Murphy et al.

(10) Patent No.: US 8,420,774 B2
(45) Date of Patent: Apr. 16, 2013

(54) DECORATING HYDROXYAPATITE BIOMATERIALS WITH MODULAR BIOLOGICALLY ACTIVE MOLECULES

(75) Inventors: William L. Murphy, Madison, WI (US); Jae Sung Lee, Madison, WI (US); Mark D. Markel, Middleton, WI (US); Ben K. Graf, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 509 days.

(21) Appl. No.: 12/628,666

(22) Filed: Dec. 1, 2009

(65) Prior Publication Data

US 2011/0129611 A1 Jun. 2, 2011

(51) Int. Cl.
*C07K 2/00* (2006.01)
*C07K 14/00* (2006.01)
*C07K 9/00* (2006.01)

(52) U.S. Cl.
USPC ........... 530/300; 530/326; 530/350; 435/69.7

(58) Field of Classification Search ........................ None
See application file for complete search history.

(56) References Cited

U.S. PATENT DOCUMENTS 7,132,506 B2 11/2006 Nishimura et al.
2008/0095817 A1 4/2008 Murphy

OTHER PUBLICATIONS

Lee et al., "Modular Peptide Growth Factors for Substrate-Mediated Stem Cell Differentiation," Angew. Chem. Int. Ed., 48(34):6266-6269 (2009).
Lee et al., "Modular Peptides Promote Human Mesenchymal Stem Cell Differentiation on Biomaterial Surfaces," Acta Biomaterialia, 2009, doi: 10.1016/j.act.bio.2009.08.003.

*Primary Examiner* — Elizabeth C Kemmerer
(74) *Attorney, Agent, or Firm* — Armstrong Teasdale LLP

(57) ABSTRACT

A modular peptide design strategy wherein the modular peptide has two functional units separated by a spacer portion is disclosed. More particularly, the design strategy combines a hydroxyapatite-binding portion and a biomolecule-derived portion. The modular peptides have improved non-covalent binding to the surface of the HA-based materials, and are capable of initiating osteogenesis, angiogenesis, and/or osteogenic differentiation.

7 Claims, 23 Drawing Sheets

SCALE BAR = 20 μm

SCALE BAR = 20 μm

SCALE BAR = 1 μm

FIG. 5A

| Gene | Primers | GenBank | bp |
|---|---|---|---|
| OCN | Fw: 5'-ggcagcgaggtagtgaagag-3'<br>Rv: 5'-ctggagaggagcagaactgg-3' | NM_199173 | 230 |
| OPN | Fw: 5'-tgaaacgagtcagctggatg-3'<br>Rv: 5'-tgaaattcatggctgtggaa-3' | X13694 | 162 |
| Cbfa1 | Fw: 5'-caccgagaccaacagagtca-3'<br>Rv: 5'-tgcttgcagccttaaactg-3' | AF053949 | 236 |
| β-actin | Fw: 5'-ggacttcgagcaagagatgg-3'<br>Rv: 5'-agcactgtgttggcgtacag-3' | NM_001101 | 234 |

SCALE BAR = 1 mm

SCALE BAR = 1 mm

SCALE BAR = 200 μm

SCALE BAR = 200 μm

SCALE BAR = 200 μm

SCALE BAR = 1 mm

SCALE BAR = 1 mm

SEQUENCE LISTING

```
<160> NUMBER OF SEQ ID NOS: 23

<210> SEQ ID NO 1
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<220> FEATURE:
<221> NAME/KEY: MOD_RES
<222> LOCATION: (5)..(5)
<220> FEATURE:
<221> NAME/KEY: MOD_RES
<222> LOCATION: (8)..(8)

<400> SEQUENCE: 1

Glu Pro Arg Arg Glu Val Ala Glu Leu
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
```

```
<222> LOCATION: (1)..(1)
<220> FEATURE:
<221> NAME/KEY: MOD_RES
<222> LOCATION: (8)..(8)

<400> SEQUENCE: 2

Glu Pro Arg Arg Ala Val Ala Glu Leu
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)

<400> SEQUENCE: 3

Glu Pro Arg Arg Ala Val Ala Ala Leu
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic

<400> SEQUENCE: 4

Glu Pro Arg Arg Glu Val Ala Glu Leu
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Glu Pro Arg Arg Ala Val Ala Glu Leu
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Glu Pro Arg Arg Ala Val Ala Ala Leu
1               5

<210> SEQ ID NO 7
<211> LENGTH: 4
<212> TYPE: PRT
<213> ORGANISM: Artificial Sequence
<220> FEATURE:
<223> OTHER INFORMATION: Synthetic

<400> SEQUENCE: 7

Ala Ala Ala Ala
1

<210> SEQ ID NO 8
```

```
<211> LENGTH: 20
<212> TYPE: PRT
<213> ORGANISM: Artificial Sequence
<220> FEATURE:
<223> OTHER INFORMATION: Synthetic

<400> SEQUENCE: 8

Lys Ile Pro Lys Ala Ser Ser Val Pro Thr Glu Leu Ser Ala Ile Ser
1               5                   10                  15

Thr Leu Tyr Leu
            20

<210> SEQ ID NO 9
<211> LENGTH: 15
<212> TYPE: PRT
<213> ORGANISM: Artificial Sequence
<220> FEATURE:
<223> OTHER INFORMATION: Synthetic

<400> SEQUENCE: 9

Lys Leu Thr Trp Gln Glu Leu Tyr Gln Leu Lys Tyr Lys Gly Ile
1               5                   10                  15

<210> SEQ ID NO 10
<211> LENGTH: 431
<212> TYPE: PRT
<213> ORGANISM: Artificial Sequence
<220> FEATURE:
<223> OTHER INFORMATION: Synthetic

<400> SEQUENCE: 10

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
```

```
                    225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
                260                 265                 270

Lys Gln Pro Phe Met Val Ala Phe Lys Ala Thr Glu Val His Phe
                275                 280                 285

Arg Ser Ile Arg Ser Thr Gly Ser Lys Gln Arg Ser Gln Asn Arg Ser
                290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
                340                 345                 350

Gly Tyr Ala Ala Tyr Tyr Cys Glu Gly Glu Cys Ala Phe Pro Leu Asn
                355                 360                 365

Ser Tyr Met Asn Ala Thr Asn His Ala Ile Val Gln Thr Leu Val His
                370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
                420                 425                 430

<210> SEQ ID NO 11
<211> LENGTH: 288
<212> TYPE: PRT
<213> ORGANISM: Artificial Sequence
<220> FEATURE:
<223> OTHER INFORMATION: Synthetic

<400> SEQUENCE: 11

Met Val Gly Val Gly Gly Gly Asp Val Glu Asp Val Thr Pro Arg Pro
1               5                   10                  15

Gly Gly Cys Gln Ile Ser Gly Arg Ala Ala Arg Gly Cys Asn Gly Ile
                20                  25                  30

Pro Gly Ala Ala Ala Trp Glu Ala Ala Leu Pro Arg Arg Arg Pro Arg
            35                  40                  45

Arg His Pro Ser Val Asn Pro Arg Ser Arg Ala Ala Gly Ser Pro Arg
50                  55                  60

Thr Arg Gly Arg Arg Thr Glu Glu Arg Pro Ser Gly Ser Arg Leu Gly
65                  70                  75                  80

Asp Arg Gly Arg Gly Arg Ala Leu Pro Gly Gly Arg Leu Gly Gly Arg
                85                  90                  95

Gly Arg Gly Arg Ala Pro Glu Arg Val Gly Gly Arg Gly Arg Gly Arg
                100                 105                 110

Gly Thr Ala Ala Pro Arg Ala Ala Pro Ala Ala Arg Gly Ser Arg Pro
            115                 120                 125

Gly Pro Ala Gly Thr Met Ala Ala Gly Ser Ile Thr Thr Leu Pro Ala
130                 135                 140

Leu Pro Glu Asp Gly Gly Ser Gly Ala Phe Pro Pro Gly His Phe Lys
145                 150                 155                 160

Asp Pro Lys Arg Leu Tyr Cys Lys Asn Gly Gly Phe Phe Leu Arg Ile
                165                 170                 175
```

His Pro Asp Gly Arg Val Asp Gly Val Arg Glu Lys Ser Asp Pro His
         180                 185                 190

Ile Lys Leu Gln Leu Gln Ala Glu Glu Arg Gly Val Val Ser Ile Lys
     195                 200                 205

Gly Val Cys Ala Asn Arg Tyr Leu Ala Met Lys Glu Asp Gly Arg Leu
     210                 215                 220

Leu Ala Ser Lys Cys Val Thr Asp Glu Cys Phe Phe Phe Glu Arg Leu
225                 230                 235                 240

Glu Ser Asn Asn Tyr Asn Thr Tyr Arg Ser Arg Lys Tyr Thr Ser Trp
                 245                 250                 255

Tyr Val Ala Leu Lys Arg Thr Gly Gln Tyr Lys Leu Gly Ser Lys Thr
                 260                 265                 270

Gly Pro Gly Gln Lys Ala Ile Leu Phe Leu Pro Met Ser Ala Lys Ser
                 275                 280                 285

<210> SEQ ID NO 12
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (25)..(25)
<223> OTHER INFORMATION: gamma-carboxylated glutamic acid
<220> FEATURE:
<221> NAME/KEY: MOD_RES
<222> LOCATION: (29)..(29)
<223> OTHER INFORMATION: gamma-carboxylated glutamic acid
<220> FEATURE:
<221> NAME/KEY: MOD_RES
<222> LOCATION: (32)..(32)
<223> OTHER INFORMATION: gamma-carboxylated glutamic acid

<400> SEQUENCE: 12

Lys Ile Pro Lys Ala Ser Ser Val Pro Thr Glu Leu Ser Ala Ile Ser
1               5                   10                  15

Thr Leu Tyr Leu Ala Ala Ala Ala Glu Pro Arg Arg Glu Val Ala Glu
             20                  25                  30

Leu

<210> SEQ ID NO 13
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (25)..(25)
<223> OTHER INFORMATION: gamma-carboxylated glutamic acid
<220> FEATURE:
<221> NAME/KEY: MOD_RES
<222> LOCATION: (32)..(32)
<223> OTHER INFORMATION: gamma-carboxylated glutamic acid

<400> SEQUENCE: 13

Lys Ile Pro Lys Ala Ser Ser Val Pro Thr Glu Leu Ser Ala Ile Ser
1               5                   10                  15

Thr Leu Tyr Leu Ala Ala Ala Ala Glu Pro Arg Arg Ala Val Ala Glu
             20                  25                  30

Leu

<210> SEQ ID NO 14

```
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (25)..(25)
<223> OTHER INFORMATION: gamma-carboxylated glutamic acid

<400> SEQUENCE: 14

Lys Ile Pro Lys Ala Ser Ser Val Pro Thr Glu Leu Ser Ala Ile Ser
1               5                   10                  15

Thr Leu Tyr Leu Ala Ala Ala Ala Glu Pro Arg Arg Ala Val Ala Ala
            20                  25                  30

Leu

<210> SEQ ID NO 15
<211> LENGTH: 33
<212> TYPE: PRT
<213> ORGANISM: Artificial Sequence
<220> FEATURE:
<223> OTHER INFORMATION: Synthetic

<400> SEQUENCE: 15

Lys Ile Pro Lys Ala Ser Ser Val Pro Thr Glu Leu Ser Ala Ile Ser
1               5                   10                  15

Thr Leu Tyr Leu Ala Ala Ala Ala Glu Pro Arg Arg Ala Val Ala Glu
            20                  25                  30

Leu

<210> SEQ ID NO 16
<211> LENGTH: 33
<212> TYPE: PRT
<213> ORGANISM: Artificial Sequence
<220> FEATURE:
<223> OTHER INFORMATION: Synthetic

<400> SEQUENCE: 16

Lys Ile Pro Lys Ala Ser Ser Val Pro Thr Glu Leu Ser Ala Ile Ala
1               5                   10                  15

Thr Leu Tyr Leu Ala Ala Ala Ala Glu Pro Arg Arg Ala Val Ala Ala
            20                  25                  30

Leu

<210> SEQ ID NO 17
<211> LENGTH: 33
<212> TYPE: PRT
<213> ORGANISM: Artificial Sequence
<220> FEATURE:
<223> OTHER INFORMATION: Synthetic

<400> SEQUENCE: 17

Lys Ile Pro Lys Ala Ser Ser Val Pro Thr Glu Leu Ser Ala Ile Ser
1               5                   10                  15

Thr Leu Tyr Leu Ala Ala Ala Ala Glu Pro Arg Arg Glu Val Ala Glu
            20                  25                  30

Leu

<210> SEQ ID NO 18
<211> LENGTH: 31
<212> TYPE: PRT
<213> ORGANISM: Artificial Sequence
<220> FEATURE:
```

<223> OTHER INFORMATION: Synthetic
<220> FEATURE:
<221> NAME/KEY: MOD_RES
<222> LOCATION: (23)..(23)
<223> OTHER INFORMATION: gamma-carboxylated glutamic acid
<220> FEATURE:
<221> NAME/KEY: MOD_RES
<222> LOCATION: (25)..(25)
<223> OTHER INFORMATION: gamma-carboxylated glutamic acid
<220> FEATURE:
<221> NAME/KEY: MOD_RES
<222> LOCATION: (30)..(30)
<223> OTHER INFORMATION: gamma-carboxylated glutamic acid

<400> SEQUENCE: 18

Lys Leu Thr Trp Gln Glu Leu Tyr Gln Leu Lys Tyr Lys Gly Ile Gly
1               5                   10                  15

Gly Gly Ala Ala Ala Ala Glu Pro Arg Arg Glu Val Ala Glu Leu
            20                  25                  30

<210> SEQ ID NO 19
<211> LENGTH: 20
<212> TYPE: PRT
<213> ORGANISM: Artificial Sequence
<220> FEATURE:
<223> OTHER INFORMATION: Synthetic

<400> SEQUENCE: 19

Lys Ile Pro Lys Ala Cys Cys Val Pro Thr Glu Leu Ser Ala Ile Ser
1               5                   10                  15

Met Leu Tyr Leu
            20

<210> SEQ ID NO 20
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: gamma-carboxylated glutamic acid
<220> FEATURE:
<221> NAME/KEY: MOD_RES
<222> LOCATION: (5)..(5)
<223> OTHER INFORMATION: gamma-carboxylated glutamic acid
<220> FEATURE:
<221> NAME/KEY: MOD_RES
<222> LOCATION: (8)..(8)
<223> OTHER INFORMATION: gamma-carboxylated glutamic acid

<400> SEQUENCE: 20

Glu Pro Pro Arg Glu Val Cys Glu Leu
1               5

<210> SEQ ID NO 21
<211> LENGTH: 20
<212> TYPE: PRT
<213> ORGANISM: Artificial Sequence
<220> FEATURE:
<223> OTHER INFORMATION: Synthetic

<400> SEQUENCE: 21

Lys Ile Pro Lys Ala Ser Ser Val Pro Thr Glu Leu Ser Ala Ile Ser
1               5                   10                  15

Thr Leu Tyr Leu
            20

-continued

```
<210> SEQ ID NO 22
<211> LENGTH: 15
<212> TYPE: PRT
<213> ORGANISM: Artificial Sequence
<220> FEATURE:
<223> OTHER INFORMATION: Synthetic

<400> SEQUENCE: 22

Lys Leu Thr Trp Gln Glu Leu Tyr Gln Leu Lys Tyr Lys Gly Ile
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic

<400> SEQUENCE: 23

Lys Leu Thr Trp Gln Glu Leu Tyr Gln Leu Lys Tyr Lys Gly Ile
1               5                   10                  15
```

DECORATING HYDROXYAPATITE BIOMATERIALS WITH MODULAR BIOLOGICALLY ACTIVE MOLECULES

STATEMENT REGARDING FEDERALLY SPONSORED RESEARCH OR DEVELOPMENT

This invention was made with government support under AR052893 awarded by the National Institutes of Health. The government has certain rights in the invention.

INCORPORATION OF SEQUENCE LISTING

A paper copy of the Sequence Listing and a computer readable form of the sequence listing containing the file named "28243-48_ST25.txt" which is 12,245 bytes in size (measured in MS-DOS) are provided herein and are herein incorporated by reference. This Sequence Listing consists of SEQ ID NOs: 1-23.

BACKGROUND OF THE DISCLOSURE

The present disclosure relates generally to hydroxyapatite (HA)-based materials coated with modular biologically active molecules such as modular peptides. Particularly preferred modular biologically active molecules may include modular cytokines, growth factors, hormones, nucleic acids, and fragments thereof. Of particular importance in this disclosure are modular growth factors having improved non-covalent binding to the surface of the HA-based materials and being capable of initiating osteogenesis, angiogenesis, and/or osteogenic differentiation.

Natural proteins often contain at least two functional domains, which are linked together to form one multi-functional protein molecule. Specifically, these proteins are capable of activating cell surface receptors, and also binding with high affinity and specificity to natural extracellular matrices (ECMs). To achieve these diverse functions, a strategy commonly employed by nature involves creating modular proteins, in which distinct domains within a single protein are designed to enable either cell signaling or ECM binding. For example, the bone ECM protein osteocalcin (OCN) binds to HA, the major mineral component in the ECM of bony tissues, with high affinity via an N-terminal domain, and also plays a critical role in regulating bone matrix formation via a C-terminal domain.

The mechanisms that enable the binding of signaling molecules to ECM in nature can potentially be extended to synthetic biomaterials as well. For example, a recent study indicated that it is possible to mimic nature's modular cell adhesion proteins (e.g. OCN, bone sialoprotein (BSP)) by engineering synthetic modular peptide molecules that bind to synthetic HA, yet remain capable of affecting cell adhesion. This modular design approach has been used to promote cell adhesion to natural and synthetic HA-based materials, which are now used in a wide range of common clinical orthopedic applications. However, previous studies have not been able to actively induce new bone formation by bone precursor cells, nor are they able to induce differentiation of stem cells into bone-forming cells.

Musculoskeletal conditions represent an average of 3% of the gross domestic product of developed countries, consuming an estimated $254 billion annually in the United States. Bone and joint diseases account for half of all chronic conditions in people over the age of 50, and the predicted doubling of this age group's population by 2020 suggests that the tremendous need for novel bone repair and replacement therapies will continue to grow rapidly. Emerging therapeutic approaches have focused on delivering growth factor molecules to skeletal defects, as these molecules are capable of actively inducing new bone formation. However, growth factor delivery strategies often result in sub-optimal delivery kinetics, and are difficult to incorporate into standard clinical procedures. These limitations complicate clinical translation of growth factor delivery in orthopedic applications.

Accordingly, there is a need in the art for modular growth factors that can be engineered to bind strongly to HA and HA-based materials, thereby forming a biologically active "molecular coating" with controllable characteristics. Specifically, it would be advantageous if the modular growth factor had two functional units, similar to natural proteins: a HA-binding sequence to allow for improved binding to the surfaces of HA and HA-based materials; and a biomolecule-derived sequence inspired by natural biologically active molecules such as bone morphogenetic protein-2 (BMP-2) and vascular endothelial growth factor (VEGF). These modular growth factors may be broadly applicable in orthopedics, as HA is among the most commonly used materials in orthopedic applications, including total joint replacements, trauma, and fracture healing.

BRIEF DESCRIPTION OF THE DISCLOSURE

Accordingly, the present disclosure is generally directed to modified peptides having improved non-covalent binding to the surfaces of a biomaterial. More specifically, in one aspect, the present disclosure is directed to a modular peptide for non-covalently binding to a surface of a HA-based biomaterial. The modular peptide comprises a hydroxyapatite-binding portion, a spacer portion, and a biomolecule-derived portion.

In some embodiments, the modular peptide is a modular growth factor such as BMP-2, BMP-7, fibroblast growth factor-2 (FGF-2), and vascular endothelial growth factor (VEGF). These modular growth factors are capable of both binding with high affinity and with spatial control to the surface of a "bone-like" HA-coated material and initiating at least one of osteogenesis, angiogenesis, and osteogenic differentiation.

In another aspect, the present disclosure is directed to a method of coating a biomaterial with a modular peptide. In one embodiment, the method comprises: exposing a biomaterial to a phosphate buffered saline (PBS) solution comprising the modular peptide.

In some embodiments, the PBS solution includes from about 100 μg to about 1500 μg. More particularly, in some embodiments the PBS solution includes from about 200 μg to about 750 μg of a modular peptide, and in some embodiments, the PBS solution includes about 500 μg of a modular peptide.

Furthermore, in some embodiments, the modular peptide is a modular growth factor such as BMP-2, BMP-7, FGF-2, and VEGF.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 5A shows the primers used in measuring the expression of osteogenic markers in Example 1.

Figure 1A:
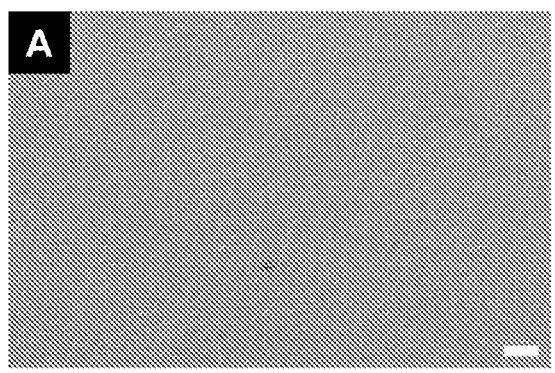
FIG. 1A shows a magnified SEM image (magnification of ×1000) of the HA-material layer grown on the PLG film in Example 1.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION OF PREFERRED EMBODIMENTS

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

The present disclosure is generally directed to a modular peptide design, and more particularly, to a modular peptide design that includes both a modular growth factor-derived portion to induce stem cell differentiation, and further, a binding portion that allows for improved binding of the modular peptides to "bone-like" HA-based coated biomaterials. The approach was designed to promote differentiation of human mesenchymal stem cells (hMSCs) into osteoblasts. MSCs are capable of differentiating into multiple cell lineages, including osteoblasts, chondrocytes and adipocytes.

Osteoblast differentiation has been shown to be regulated by multiple proteins, including bone morphogenetic proteins (BMPs) and Wnt. Among them, BMP-2 is one of the most potent inducers of osteogenic MSC differentiation in vitro and in vivo. BMP-2 promotes osteogenic differentiation by up-regulation expression of bone-related proteins, including osteocalcin (OCN), osteopontin (OPN), and alkaline phosphatase (ALP).

Based on the multifunctional properties of natural skeletal proteins (e.g., osteocalcin) and the inductive effects of BMP-2 on hMSC differentiation, a modular peptide design strategy that has two functional units has been developed. More particularly, the design strategy combines a HA mineral binding portion (also referred to herein as hydroxyapatite-binding portion) and a biomolecule-derived portion has now been found. It was further found that binding to HA-based biomaterials, and subsequent release, could be varied significantly by changing the sequence of the hydroxyapatite-binding portion.

The first unit of the modular peptide includes a peptide sequence inspired by an N-terminal α-helix in the protein osteocalcin (OCN), which is known to bind strongly to the crystal lattice of HA-mineral. Hydoxyapatite (HA) is a major mineral component of vertebrate bone tissue and has been widely used in orthopedic applications since the early 1980s due to its favorable interactions with native bone tissue, which is often termed "bioactivity." Specifically, HA has been used clinically as a bone void filler, a non-load-bearing implant (e.g., for nasal septal bone and middle ear), and as a coating on metallic implants to promote their fixation to bone and limit the need for cemented fixation. In each case, the goal of these devices is to promote bone growth upon or within an implant, and HA encourages the process by promoting proliferation and matrix synthesis by bone-forming cells.

Preferably, the first hydroxyapatite-binding portion (e.g., SEQ ID NO:1) includes a peptide sequence inspired by the 5.7 kDa native protein osteocalcin (OCN), and more specifically, by the 9-mer sequence on the N-terminus of OCN. Osteocalcin-HA binding is largely mediated via the peptide sequence of OCN, which contains three γ-carboxylated glutamic acid (Gla) residues at positions 1, 5, and 8 that coordinate with calcium ions in the HA crystal lattice to promote high levels of binding.

Alternatively, it has been found that at least one or all three Gla residues present in SEQ ID NO:1 can be substituted with either glutamic acid (Glu) or alanine (Ala). Specifically, in some embodiments, the peptide sequences of SEQ ID NO:2 (γ-carboxylated glutamic acid (Gla) residues at positions 1 and 8 and Ala residue at position 5); SEQ ID NO:3 (γ-carboxylated glutamic acid (Gla) residue at position 1 and Ala residues at positions 5 and 8); SEQ ID NO:4 (Glu residues at positions 1, 5, and 8); SEQ ID NO:5 (Glu residues at positions 1 and 8 and Ala residue at position 5); and SEQ ID NO:6 (Glu residue at position 1 and Ala residues at positions 5 and 8) may be used as the hydroxyapatite-binding portion (see Table 1). The Glu and Ala substitutions can influence the charge density and secondary structure of the peptide molecules, and therefore, influence the peptide-HA binding.

TABLE 1

Sequences of Glu and Ala substituted hydroxyapatite-binding portion of OCN 9-mer.

| SEQ ID NO | Peptide | Amino Acid Sequence |
|---|---|---|
| 1 | γ-carboxylated glutamic acid (Gla) residues at positions 1, 5, and 8 | γEPRRγEVAγEL |
| 2 | γ-carboxylated glutamic acid (Gla) residues at positions 1 and 8 and Ala residue at position 5 | γEPRRAVAγEL |
| 3 | γ-carboxylated glutamic acid (Gla) residue at position 1 and Ala residues at positions 5 and 8 | γEPRRAVAAL |
| 4 | Glu residues at positions 1, 5, and 8 | EPRREVAEL |
| 5 | Glu residues at positions 1 and 8 and Ala residue at position 5 | EPRRAVAEL |
| 6 | Glu residue at position 1 and Ala residues at positions 5 and 8 | EPRRAVAAL |

The modular peptide further includes a second unit that is a biomolecule-derived portion capable of initiating at least one of osteogenesis, angiogenesis, and osteogenic differentiation. For example, in one preferred embodiment, the second unit is a biomolecule-mimic portion derived from the 20-mer "knuckle" epitope of BMP-2 protein (SEQ ID NO:8), disclosed in U.S. Pat. No. 7,132,506 to Kyocera Corporation (Nov. 7, 2006). Specifically, it has been previously found that various forms of BMP-2 are capable of enhancing bone formation at ectopic and orthopic sites, including recombinant BMP-2 protein delivered exogenously and BMP-2 protein synthesized in vivo upon expression of BMP-2 encoding DNA. BMP-2 has also become an important component of emerging stem cell-based tissue regeneration approaches, as stem cell fate decisions are often regulated by growth factor signaling. For example, BMP-2 has been shown to promote differentiation of human mesenchymal stem cells down the osteogenic lineage in standard pro-osteogenic cell culture conditions.

Another suitable growth factor includes the 15-mer sequence derived from VEGF (SEQ ID NO:9). Other suitable growth factors that can be used in the biomolecule-derived portion (i.e., second unit) of the modular peptide include sequences derived from BMP-7 (SEQ ID NO:10) and FGF-2 (SEQ ID NO:11).

To control the spacing between the HA-binding portion and the biomolecule-derived portion, a spacer portion is present in the modular peptide. It is believed that the bioactivity of the biomolecule-derived portion in the modular peptide may be increased with an increase in the spacer length. More particularly, it is hypothesized that too little of a spacing between the surface of the biomaterial and the biomolecule-derived portion may not be optimal for the biomolecule-derived portion's bioactivity as the biomolecule-derived portion may be so close to the surface so as not to be readily accessible to other cell receptors. Accordingly, by controlling the spacing between the HA-binding portion and the biomolecule-derived portion, the level of bioactivity by the biomolecule-derived portion can be controlled. Generally, the spacer portion can be any amino acid sequence capable of forming an α-helix with the HA-binding portion. For example, in one or more embodiments, the spacer portion may be an alanine $(Ala)_n$ spacer, such as the $(Ala)_4$ spacer having the sequence of SEQ ID NO:7. This spacer portion is particularly preferred for use as it is capable of being both a spacer and an extension, as the HA-binding portion and poly (Ala) sequences have a known propensity to form α-helices. Other suitable spacer portions may include a leucine $(Leu)_n$ spacer, a lysine $(Lys)_n$ spacer, and a glutamate $(Glu)_n$ spacer.

Other suitable spacer portions may include a polyethylene glycol spacer such as 3500 Da polyethylene glycol and 5000 Da polyethylene glycol.

The modular peptides of the present disclosure may be synthesized by standard solid-phase synthesis, such as by using Fmoc-protected amino acids and purified by HPLC. For example, in one embodiment, the modular peptides are synthesized by solid-phase peptide synthesis on Fmoc-Rink Amide MBHA resin with Fmoc-protected α-amino groups via peptide synthesizer (CS Bio, Menlo Park, Calif.). The side-chain-protecting groups used can be: t-butyl for Tyr, Thr and Ser; 2,2,5,7,8-pentamethyl-chroman-6-sulfonyl for Arg; t-BOC for Lys; and t-butyl ester for Gla and Glu. In some cases, 5(6)-FAM (5(6)-carboxyfluorescein, Sigma) is conjugated to the N-terminal lysine residue to characterize binding and release kinetics of modular growth factors on HA-coated biomaterials. The resulting peptide molecules can be cleaved from resin for 4 hours using a TFA:TIS:water (95:2.5:2.5) cocktail solution, filtered to remove resin, and precipitated in diethyl ether. Crude peptide mixtures can be purified using a Shimadzu Analytical Reverse Phase-HPLC (Vydac C18 column) with 1%/min of 0.1% TFA in acetonitrile (ACN) for 60 minutes.

It should be understood by one skilled in the art that various other known methods for preparing modular peptides can also be used without departing from the scope of the present disclosure. For example, in one alternative embodiment, the modular peptides are synthesized manually with PyBop/DIPEA/HOBT activation.

Suitable modular peptides of the present disclosure include those having a sequence selected from SEQ ID NO:12, SEQ ID NO:13, SEQ ID NO:14, SEQ ID NO:15, SEQ ID NO:16, SEQ ID NO:17, and SEQ ID NO:18.

The present disclosure is further directed to methods of coating biomaterials with the modular peptides described above. Generally, a biomaterial, such as hydroxyapatite or hydroxyapatite-based materials, is coated by exposing the biomaterial to a solution including the modular peptide. In one embodiment, the biomaterial is exposed to the solution using a dip coating method. Other suitable methods for exposing the biomaterial to a solution including the modular peptide include spotting, stamping, brushing, and painting.

Figure 6:
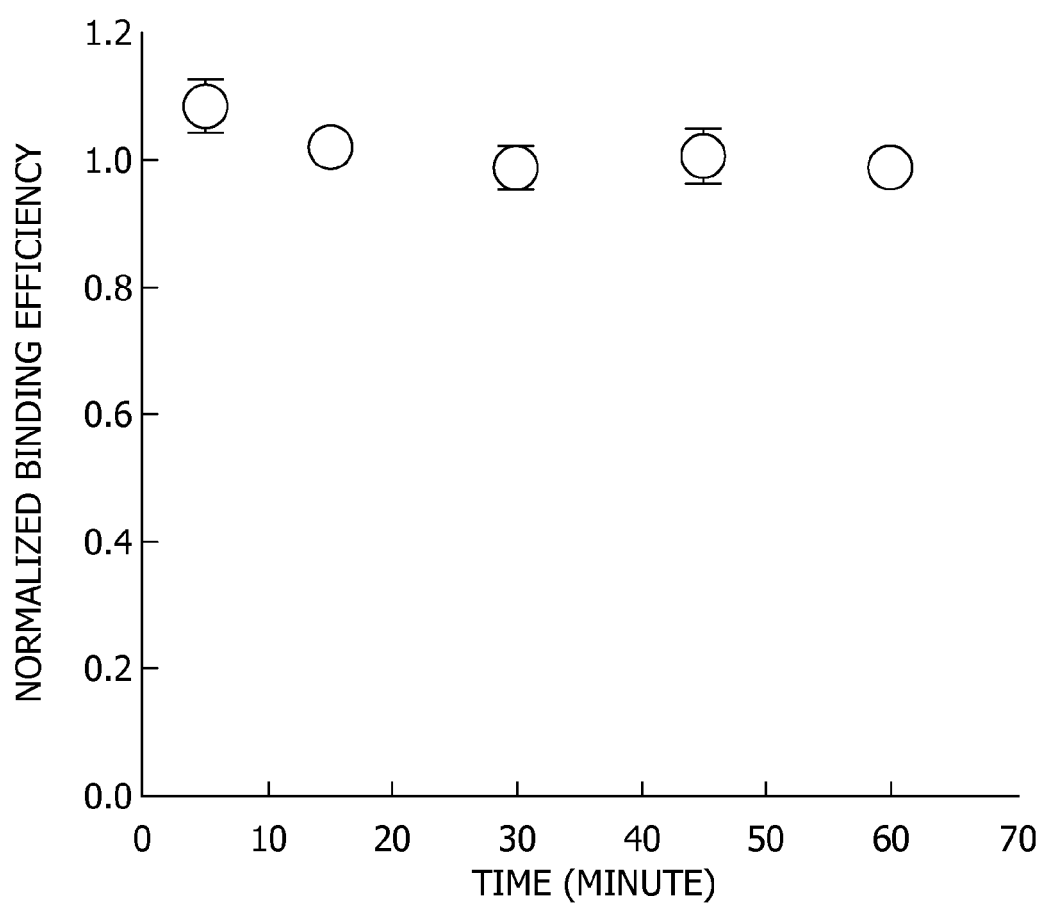
FIG. 6 shows the binding isotherm of modular eBGa3 peptide to HA particles over time at 37° C. as measured in Example 1.

For example, in one or more embodiments, a hydroxyapatite-based material is exposed to a phosphate buffered solution (PBS) including from about 200 µg to about 750 µg of a modular peptide. More particularly, the PBS solution included from about 200 µg to about 750 µg of a modular peptide having a sequence selected from SEQ ID NO:12 (γ-carboxylated glutamic acid (Gla) residues at positions 25, 29, and 32), SEQ ID NO:13 (γ-carboxylated glutamic acid (Gla) residues at positions 25 and 32 and Ala residue at position 29), SEQ ID NO:14 (γ-carboxylated glutamic acid (Gla) residue at position 25 and Ala residues at positions 29 and 32), SEQ ID NO:15 (Glu residues at positions 25 and 32 and Ala residue at position 29), SEQ ID NO:16 (Glu residue at position 25 and Ala residues at positions 29 and 32), SEQ ID NO:17 (Glu residues at positions 25, 29 and 32), or SEQ ID NO:18 Glu residues at positions 23, 27, and 30). In one particular embodiment, HA particles were exposed to SEQ ID NO:12 in 10 µM PBS peptide solution (pH 7.4) for a period of 60 minutes. The amount of peptide bound on the HA particles was normalized by the mean of all values, and the results are shown in FIG. 6.

It should be noted that although discussed herein using a PBS solution, any carrier solution known in the art for including a modular peptide can be used in the methods of the present disclosure. For example, other suitable solutions include HEPES buffer solution, PIPES buffer solution, Tris buffer solution, saline solution, and the like.

Typically, the biomaterial is exposed to the solution including the modular peptide under constant agitation.

To ensure sufficient coating of the biomaterial, it is suitable to expose the biomaterial to the solution including the modular peptide for a period of at least two minutes, and more suitably, at least about 1 hour. More suitably, the biomaterial is exposed to the solution for a period of from about two minutes to about 10 hours. In one particular embodiment, the biomaterial is exposed for a period of about 4 hours.

The disclosure will be more fully understood upon consideration of the following non-limiting Examples.

EXAMPLE 1

In this Example, modular peptides are synthesized and used to coat a HA-based biomaterial. The binding efficiency and subsequent release of the modular peptides from the biomaterial is then analyzed. Additionally, the bioactivity of the biomolecule-derived portion used in the modular peptide is analyzed.

Synthesis and Purification of Modular Growth Factors

To begin, multiple modular peptides (Table 2) were synthesized by solid-phase peptide synthesis on Fmoc-Rink Amide MBHA resin with Fmoc-protected α-amino groups via peptide synthesizer (CS Bio, Menlo Park, Calif.). The side-chain-protecting groups used were: t-butyl for Tyr, Thr and Ser; 2,2,5,7,8-pentamethyl-chroman-6-sulfonyl for Arg; t-BOC for Lys; and t-butyl ester for Gla and Glu. In some cases, 5(6)-FAM (5(6)-carboxyfluorescein, Sigma) was conjugated to the N-terminal lysine residue to characterize binding and release kinetics of modular growth factors on HA-coated polylactide-co-glycolide (PLG) films. The resulting peptide molecules were cleaved from resin for 4 hr using a TFA:TIS:water (95:2.5:2.5) cocktail solution, filtered to remove resin, and precipitated in diethyl ether. Crude peptide mixtures were purified using a Shimadzu Analytical Reverse Phase-HPLC (Vydac C18 column) with 1%/min of 0.1% TFA in acetonitrile (ACN) for 60 minutes and analyzed by MALDI-TOF mass spectrometry (Bruker Reflex II time-of-flight mass spectrometer).

TABLE 2

Sequences of modular peptide growth factors and natural template.

| Peptide | Amino Acid Sequence |
|---|---|
| Human BMP-2 | KIPKACCVPTELSAISMLYL (AAs: 73-92) (SEQ ID NO: 19) |
| Human OCN | γEPRRγEVCγEL (AAs: 17-25) (SEQ ID NO: 20) |
| eBMP2[a] | KIPKASSVPTELSAISTLYL (SEQ ID NO: 21) |
| eBGa3[b] | KIPKASSVPTELSAISTLYLAAAAγEPRRγEVAγEL (SEQ ID NO: 12) |
| eBGa2 | KIPKASSVPTELSAISTLYLAAAAγEPRRAVAγEL (SEQ ID NO: 13) |
| eBGa1 | KIPKASSVPTELSAISTLYLAAAAγEPRRAVAAL (SEQ ID NO: 14) |
| eBGu1 | KIPKASSVPTELSAIATLYLAAAAEPRRAVAAL (SEQ ID NO: 16) |
| eBGu3 | KIPKASSVPTELSAISTLYLAAAAEPRREVAEL (SEQ ID NO: 17) |

[a]The eBMP2 peptide sequence was originally synthesized by Tanihara and co-workers. Cys and Met from human BMP-2 sequence were replaced by Ser and Thr.
[b]Cys from human OCN sequence was replaced by Ala in modular peptides to avoid complicating disulfide linkages.

PLG Film Preparation and Mineral Growth

Poly (lactide-coglycolide) (PLG) films were prepared via a solvent casting process in which PLG (85:15) pellets were dissolved in chloroform (50 mg/ml), added to a PTFE dish, and dried for 2 days. The films were further dried at 50~55° C. for 4 hr to remove residual solvent and samples were cooled to room temperature. Square films (1 cm$^2$) were manually cut out of the resulting PLG film sheets. A "bone-like" HA-based material layer was grown on the PLG films using a direct deposition technique by biomimetic mineralization in modified simulated body fluid (mSBF).

The surface morphologies of HA-coated and uncoated PLG films were examined by scanning electron microscopy (SEM). A conductive gold coating was applied to the surface of each film via sputter coating, and samples were imaged under high vacuum using a LEO 1530 SEM (Zeiss, Oberkochen, Germany) operating at 10-30 kV. X-ray diffraction spectra of HA-coated and non-coated PLG films were collected using a Bruker Hi-Star 2-D X-ray diffractometer (XRD).

Binding Isotherms and Release Kinetics of Modular Peptides

To measure the binding efficiency of modular peptides to the HA-coated PLG films and to gain preliminary insight into the properties that influence modular peptide immobilization, we first exposed 1 cm$^2$ HA-coated PLG films to PBS solutions containing 500 μg (1 mg/ml) of 5(6) FAM-conjugated eBMP-2, eBGu1, eBGu3, eBGa1, or eBGa3 modular peptide solution (See Table 1 for definitions of these abbreviations). The films were incubated in peptide solutions with constant agitation for 4 hours at 37° C., and the amount of free peptide remaining was determined by measuring the fluorescence emission of the solution (excitation: 494 nm; emission 519 nm) using a Synergy HT Multi-Detection Microplate Reader (BioTek, Winooski, Vt.), and comparing this emission to standard samples with known concentrations of 5(6)-FAM. To further characterize surface immobilization of the peptide with the highest binding efficiency—the eBGa3 peptide—1 cm$^2$ HA-coated films were incubated in various concentrations (50-750 μM) of 5(6)-FAM-conjugated eBGa3 peptide for 4 hours with constant agitation at 37° C. The amount of peptide bound to HA-coated film was again determined by fluorescence analysis, as described above.

To quantify release kinetics of 5(6) FAM-conjugated modular peptides from HA-coated film, the films were first incubated in solutions containing 250 μM (~500 μg) of each peptide (eBGu1, eBGu3, eBGa1, or eBGa3) to allow for binding (as described above), then incubated in 500 μl of PBS buffer at 37° C. with constant agitation for 5 days (eBGu1 and eBGu3 peptides) or 10 weeks (eBGa1 and eBGa3 peptides), respectively. Whole buffer solutions were changed at indicated time points and the amount of peptide released from the HA-coated film was determined via fluorescence analysis and comparison with standards containing known amounts of 5(6)-FAM. The fluorescent images of fluorescently-labeled peptides bound to HA-coated films were obtained using an Olympus IX51 fluorescence microscope (Olympus, Center Valley, Pa.).

Culture of Human Mesenchymal Stem Cells (hMSCs)

hMSCs (Cambrex, Walkersville, Md., passages 5-6) were cultured in mesenchymal stem cell growth medium (MSCGM: Cambrex) consisting of MSC Basal Medium supplemented with 10% fetal bovine serum, L-glutamine, 100 units/ml penicillin, and 0.1 mg/ml streptomycin and grown using culture methods described elsewhere. 2.5×10$^4$ hMSCs were seeded onto either tissue culture-treated polystyrene (TCP) or four different types of experimental substrates (1 cm$^2$) (PLG, HA-coated PLG, eBGu3-treated HA coating, or eBGa3-treated HA coating). hMSCs were allowed to attach to each substrate overnight, then cultured in MSCGM with osteogenic culture supplements (OS) (0.1 μM dexamethasone, 50 μg/ml ascorbic acid, and 10 mM β-glycerophosphate) for 24 days. The effects of soluble peptides included in culture medium were evaluated by adding 50 μg of eBGu3 or eBGa3 peptides to hMSC cultures on TCP in 500 μl of medium with or without osteogenic culture supplements. In each experimental and control sample, whole volume medium changes were performed every 4 days by replacement with fresh medium and collected medium was used for BMP-2 and OCN ELISA assays.

Quantification of Alkaline Phosphatase (ALP) Activity

The biological activity of modular peptides was initially assayed by their ability to enhance ALP activity in hMSCs. AP Assay Reagent S (GenHunter, Nashville, Tenn.) was used for cell staining and the EnzoLyte pNPP Alkaline Phosphatase Assay Kit (Anaspec, San Jose, Calif.) was used to measure enzymatic activity of ALP at day 12. For ALP staining, cells were washed with 1 ml of 1×PBS and 10% formalin, incubated at room temperature for 30 minutes, and washed again with PBS, and this wash was repeated 3 times. Cell layers were then stained with 0.5 ml of AP Assay Reagent S and incubated at room temperature for 30 minutes. Cell layers were washed 3 times with 1×PBS after staining was completed. Images of stained samples were captured via an Olympus IX-51 inverted microscope. For the ALP activity assay, cells were washed twice with a lysis buffer containing 0.1% Triton X-100. The lysate was centrifuged, and the resulting supernatant was assayed for ALP activity by incubating with 50 μl p-nitrophenyl phosphate (pNPP) in an assay buffer at 37° C. for 15 minutes. ALP activity was measured at 405 nm, and calculated as the ratio of p-nitrophenol released to total DNA concentration (nmol/min/μg DNA). To determine the amount of total DNA in each well, the cell nuclei were disrupted by addition of the aforementioned lysis buffer followed by centrifugation, and quantified using the CyQUANT Assay Kit (Molecular Probes, Eugene, Oreg.).

Characterization of Mineralized Tissue Formation

Characterization of mineralized tissue growth was performed via Alizarin Red-S (ARS) staining at day 20. The cultured cells on each type of biomaterial were washed with PBS and fixed in 10% (v/v) formaldehyde at room temperature for 30 minutes. The cells were then washed twice with excess distilled H$_2$O prior to addition of 1 ml of 40 mM ARS (pH 4.1) per well for 30 minutes. After aspiration of the unincorporated ARS, the wells were washed four times with 4 ml distilled H$_2$O while shaking for 10 minutes. For quantification of staining, 400 μl 10% (v/v) acetic acid was added to each well for 30 minutes with shaking. The cell monolayers were then scraped from the substrates and transferred with 10% (v/v) acetic acid to a 1.5-ml tube. After vortexing for 30 seconds, the slurry was overlaid with 250 μl mineral oil, heated to 85° C. for 10 minutes, and transferred to ice for 5 minutes. The slurry was then centrifuged at 15,000 g for 15 minutes and 300 μl of the supernatant was removed to a new 1.5-ml tube. Then 200 μl of 10% (v/v) ammonium hydroxide was added to neutralize the acid. Aliquots (100 μl) of the supernatant were read in triplicate at 405 nm in 96-well plate reader.

BMP-2 and Osteocalcin ELISAs

Two ELISA kits were used to quantify the secreted amount of BMP-2 (Quantikine BMP-2 Immunoassay, R&D Systems, Minneapolis, Minn.) and osteocalcin (Gla-type Osteocalcin EIA Kit, Zymed, Carlsbad, Calif.) in culture media according to manufacturers instructions. Cell culture media were collected from various culture conditions at days 8, 16, and 24 and then measured for BMP-2 and osteocalcin protein levels.

RNA Purification and RT-PCR Analysis

For mRNA analysis, the adherent cells were removed from culture dishes or each cultured substrate via 0.05% trypsin and resuspended in 350 µl RLT buffer (Qiagen, Valencia, Calif.). Total RNA was extracted using RNeasy mini-kits (Qiagen). First-strand cDNA was synthesized from 0.5 µg total RNA with 0.5 µg pd(T)$_{12-18}$ as the first strand primer, using Ready-to-Go RTPCR Beads (GE Healthcare, Piscataway, N.J.), and then amplified by PCR using primer sets (FIG. 5A) in a Robocycler Gradient 96 (Stratagene, La Jolla, Calif.). Cycling conditions were as follows: 97° C. for 5 minutes followed by 32 cycles of amplification (95° C. denaturation for 30 seconds, 60° C. annealing for 30 seconds, 72° C. elongation for 30 seconds), with a final extension at 72° C. for 5 minutes. The PCR products were analyzed by electrophoresis on a 1.5% agarose gel stained with SYBR gold nucleic acid gel stain and relative gene ratios of OCN, OPN, and Cbfa1 versus-actin gene were measured by densitometry.

Statistical Analysis

All data are given as mean±standard deviation. Statistical comparisons of the results were made using one way analysis of variance (ANOVA) with Dunnett's post hoc tests. Shapiro-Wilk method was used if a normality test was needed. The data analyses were performed with Statistical Program for the Social Sciences (SPSS) software and differences were considered significant at p<0.05 between control and experimental groups.

Results

Modular Peptide Binding and Release Kinetics

Figure 1B:
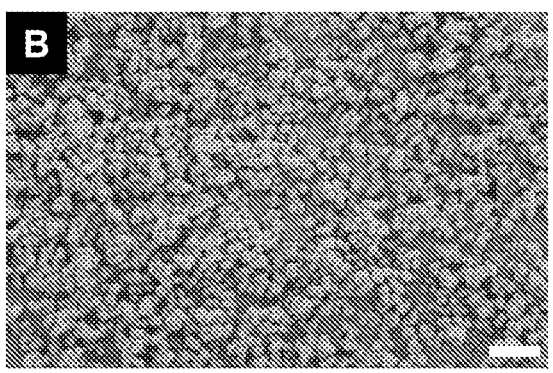
FIG. 1B shows a magnified SEM image (magnification of ×1500) of the HA-material layer grown on the PLG film in Example 1.
Figure 1C:
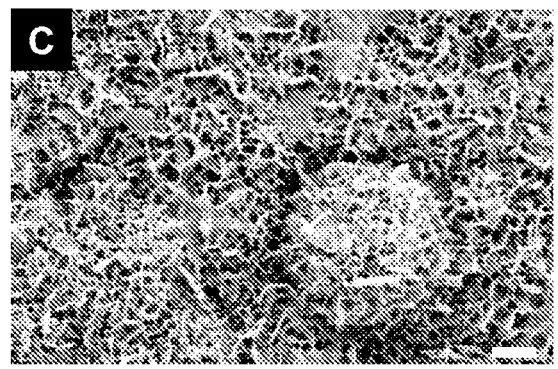
FIG. 1C shows a magnified SEM image (magnification of ×30000) of the HA-material layer grown on the PLG film in Example 1.
Figure 1D:
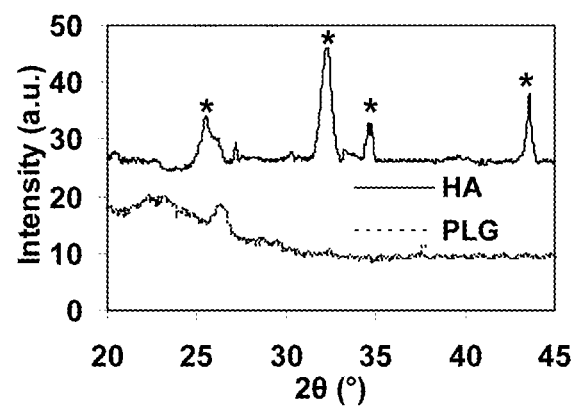
FIG. 1D shows a XRD spectra of the HA-material layer grown on the PLG film in Example 1.

Specifically, SEM images (FIG. 1A-C) and XRD spectra FIG. 1D) demonstrated that the HA-mineral layer grown on the PLG film surface had a plate-like nanostructure and a HA phase, similar to vertebrate bone mineral in structure and composition.

Figure 2A:
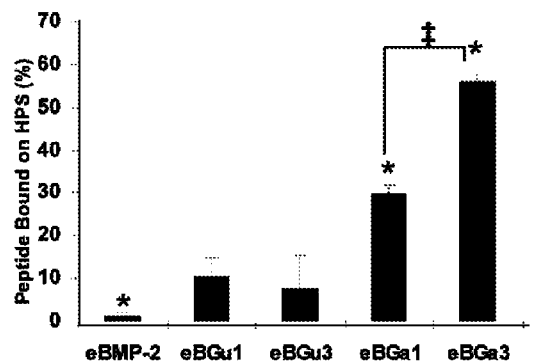
FIG. 2A shows the binding efficiency of the various modular peptides of Example 1 on the HA-coated PLG films.
Figure 2B:
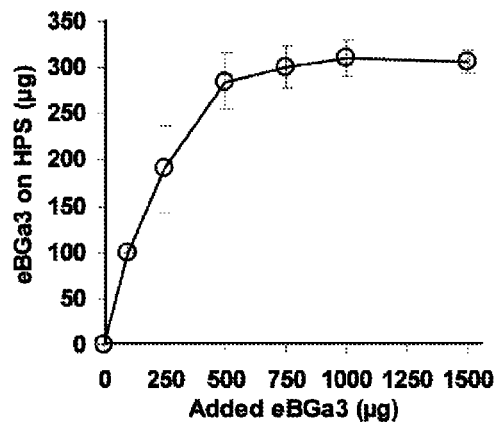
FIG. 2B shows the binding isotherm of eBGa3 of Example 1 on the HA-coated PLG films as a function of peptide concentration.
Figure 2C:
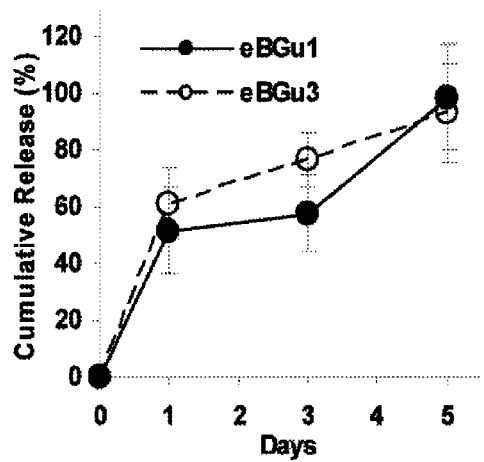
FIG. 2C shows the release kinetics of eBGu1 and eBGu3 of Example 1 on the HA-coated PLG films.
Figure 2D:
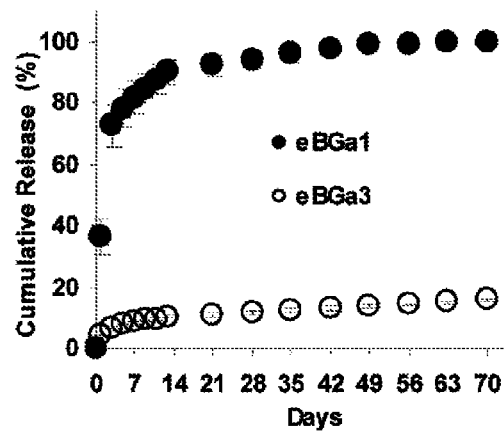
FIG. 2D shows the release kinetics of eBGa1 and eBGa3 of Example 1 on the HA-coated PLG films.

The binding efficiency of modular peptides on the HA-coated PLG films was sequence-dependent and increased in the following order: eBGu3 (7.6±7.8%)<eBGu1 (10.3±4.7%)<eBGa1 (29.9±2%)<eBGa3 (55.9±2.2%) (FIG. 2A). The binding efficiency of eBGa3 was substantially higher than other peptides studied (p*‡<0.005), and the binding of this molecule was thus studied in further detail. The amount of bound eBGa3 on the HA-coated film increased with peptide concentration and reached saturation at approximately 150 µM (300 µg) (FIG. 2B). The release kinetics of the modular peptides from HA-coated films were also highly dependent on the HA-binding portion (FIGS. 2C and D). eBGu1 (98.89±18.84% after 5 days) and eBGu3 (93.33±17.24% after 5 days) peptides were released rapidly from HA-coated films. In contrast, the eBGa3 peptide was released much more slowly, as only 15.7±0.6% of peptide was released after 70 days (FIG. 2D). Notably, these data indicate that nearly 85% of the initially bound eBGa3 peptide remained bound after 70 days.

Biological Activity of Modular Peptides

Figure 3A:
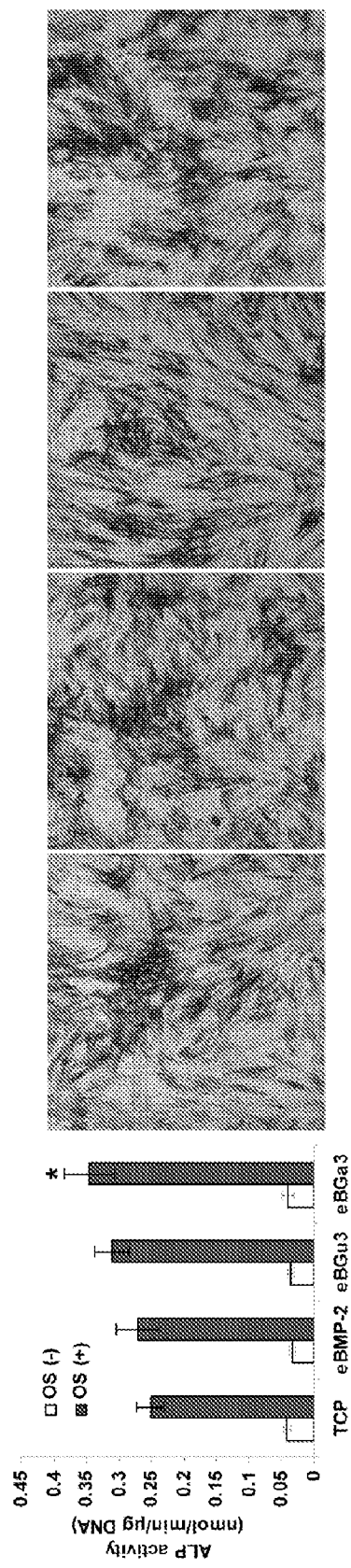
FIG. 3A shows the effect of soluble modular peptides on ALP activity in hMSCs as measured in Example 1.
Figure 3B:
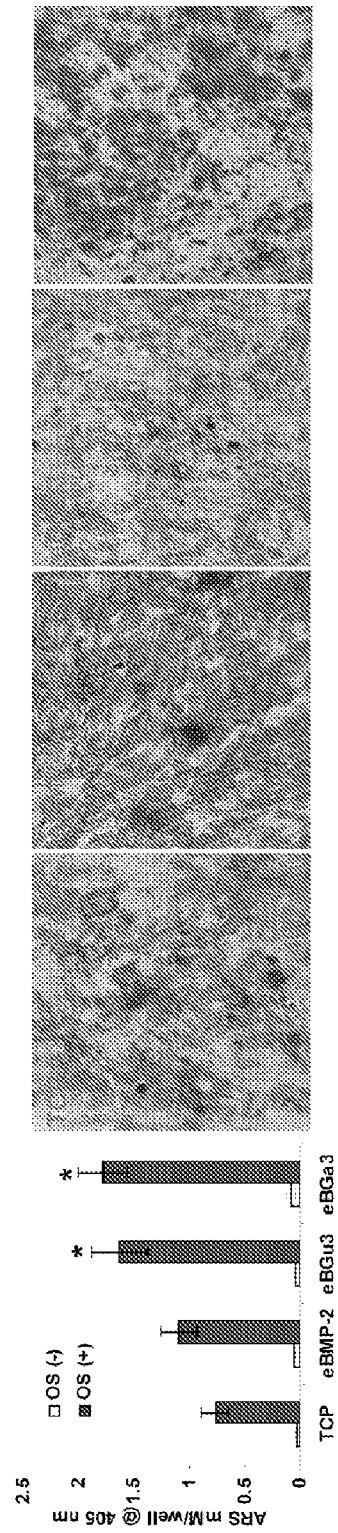
FIG. 3B shows the effect of soluble modular peptides on mineralized tissue formation in hMSCs as measured in Example 1.

Soluble modular peptides added to hMSC growth medium along with osteogenic supplements had a positive influence on osteogenic differentiation of hMSCs. Specifically, the eBGa3 peptide significantly increased ALP activity (p=0.017) (FIG. 3A) and mineralized tissue formation (p=0.018) (FIG. 3B). Importantly, there were no significant differences between the positive effects of eBGu3 and eBGa3 when added as soluble supplements to standard hMSC culture, suggesting that the biological activity of the BMP2-derived portion of the peptides was not significantly influenced by the sequence of the HA-binding portion.

Figure 4A:
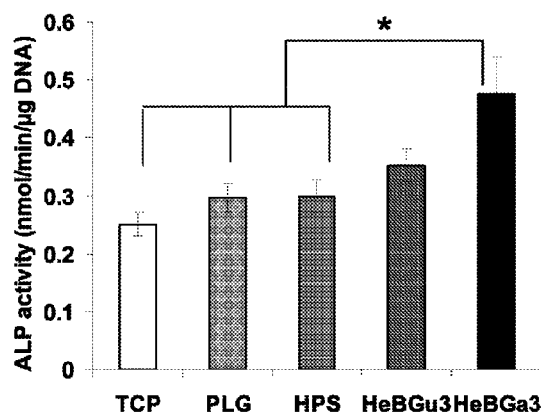
FIG. 4A shows the effect of immobilized modular peptides on ALP activity in hMSCs as measured in Example 1.
Figure 4B:
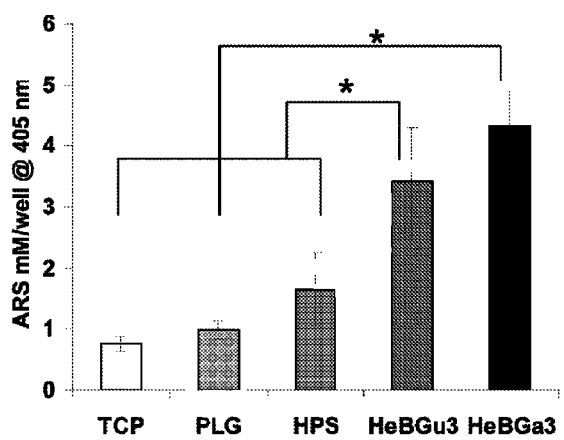
FIG. 4B shows the effect of immobilized modular peptides on mineralized tissue formation in hMSCs as measured in Example 1.
Figure 4C:
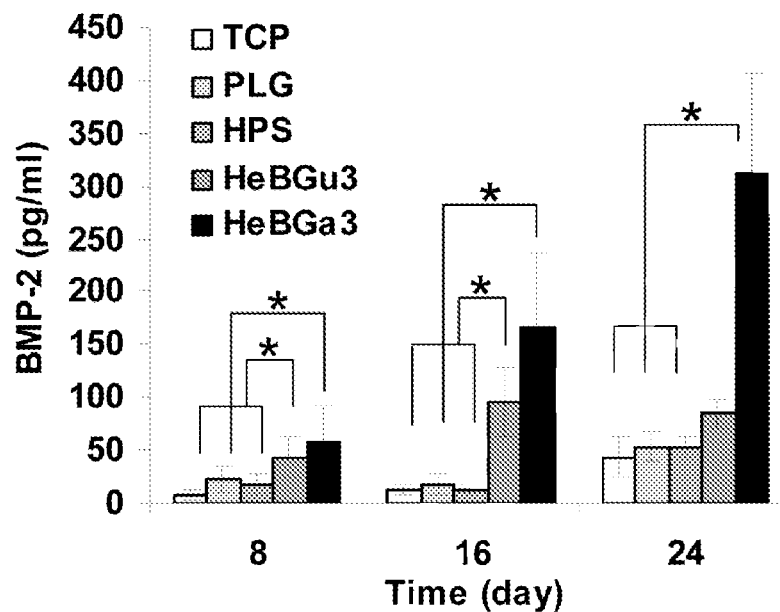
FIG. 4C shows the effect of immobilized modular peptides on BMP-2 secretion by hMSCs as measured in Example 1.
Figure 4D:
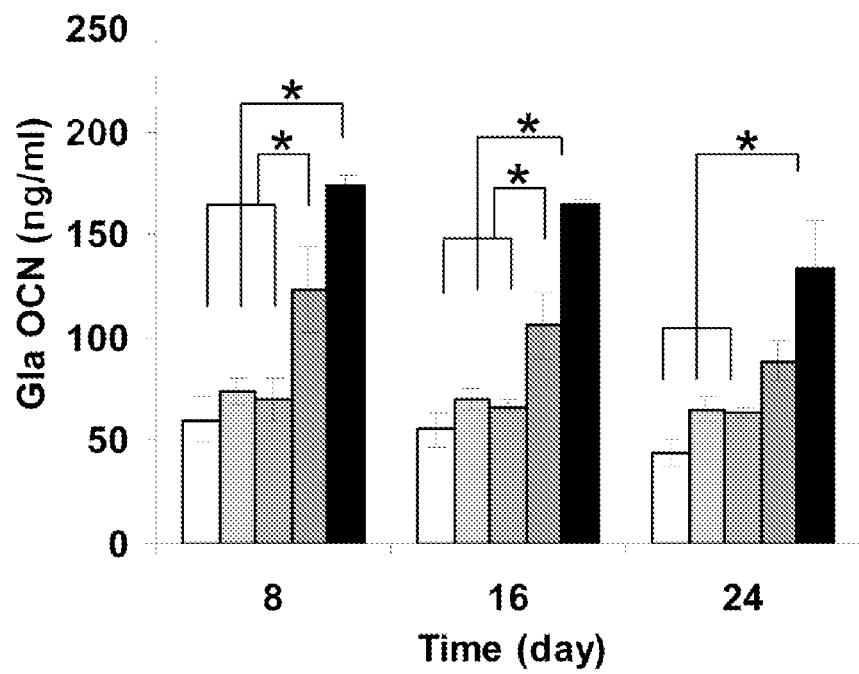
FIG. 4D shows the effect of immobilized modular peptides on OCN production by hMSCs as measured in Example 1.

When bound to a HA-coated film, the eBGa3 peptide significantly enhanced ALP activity and mineralized tissue formation by hMSCs (FIGS. 4A and B). hMSCs cultured on eBGa3-bound, HA-coated films (termed "HeBGa3 substrates") expressed significantly higher ALP activity (0.48±0.06 nmol/min/µg DNA) than hMSCs on untreated TCP (0.25±0.02), PLG (0.30±0.02), or HA-coated (0.30±0.03) films (FIG. 4A). Similarly, Alizarin red S staining of mineralized tissue was significantly increased on HeBGa3 substrates (4.32±0.57 mM/well) when compared to untreated TCP (0.76±0.12), PLG (0.98±0.14), or HA-coated (1.66±0.6) substrates (FIG. 4B). Importantly, HeBGa3 film substrates also induced enhanced BMP-2 secretion (FIG. 4C, days 16 and 24) and OCN production (FIG. 4D, days 8, 16, and 24) when compared to untreated substrates. Specifically, the hMSCs cultured on HeBGa3 produced a 6-fold higher amount of BMP-2 protein (311.59±94.55 pg/ml) when compared to TCP (43.36±18.60 pg/ml) at day 24 (p=0.002) (FIG. 4C), and OCN production was approximately 3-fold higher on HeBGa3 substrates (172.98±5.7 ng/ml) when compared to TCP substrates (60.21±10.62 ng/ml) on day 8 (p<0.0001) (FIG. 4D). Taken together, these data indicate that the eBGa3-treated substrates promote osteogenic differentiation of hMSCs.

The effects of eBGu3-treated, HA-coated films (termed "HeBGu3 substrates") on osteogenic differentiation of hMSCs were less pronounced than the effects of the HeBGa3 substrates. Specifically, HeBGu3 substrates did not significantly enhance ALP activity of hMSCs (FIG. 4A), but did significantly enhance mineralized tissue formation (p<0.02) (FIG. 4B). Effects of HeBGu3 substrates on production of BMP2 and OCN were significant at day 8 and day 16, but not significant at day 24. These data indicate that the eBGu3-treated substrates can promote osteogenic differentiation of hMSCs, but the effects are not as substantial as the effects of eBGa3-treated substrates.

Expression of Osteogenic Markers

Figure 5B:
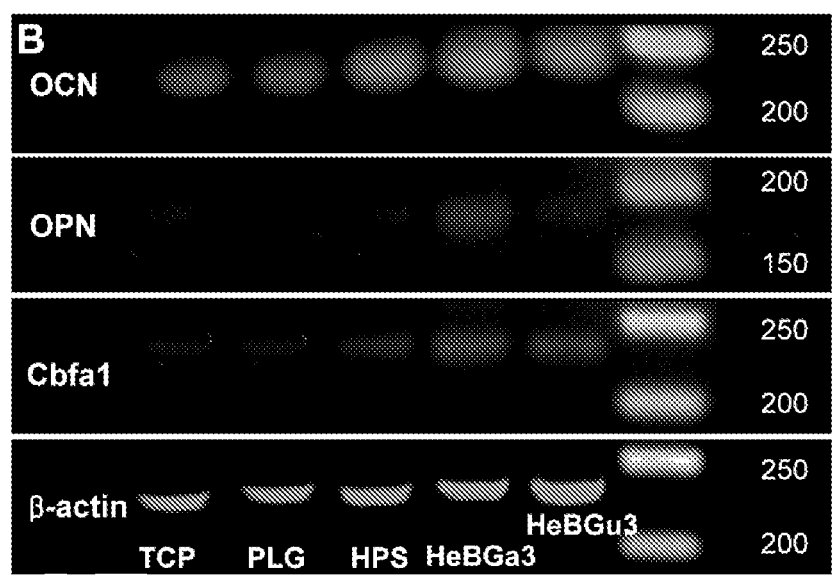
FIG. 5B shows the effect of the immobilized modular peptides on expression of osteogenesis-related genes in hMSCs as measured in Example 1.
Figure 5C:
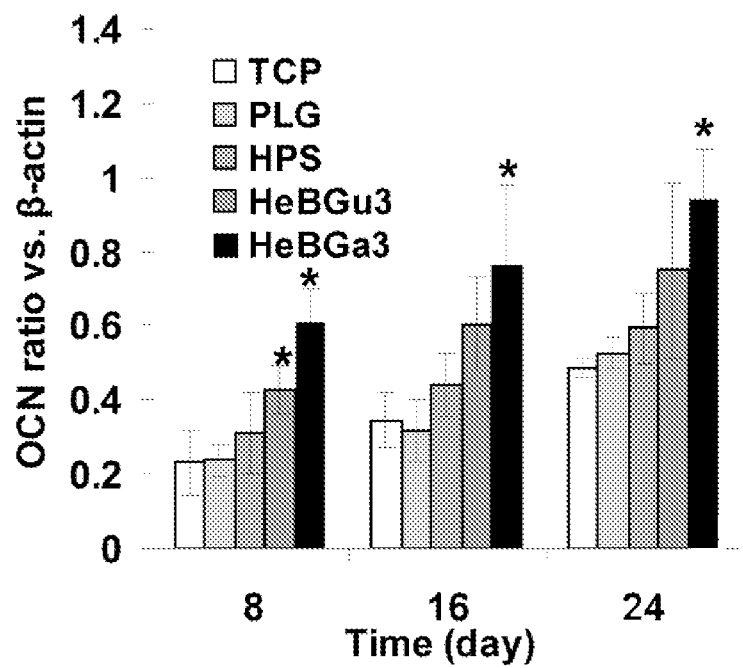
FIG. 5C shows the effect of the immobilized modular peptides on OCN expression in hMSCs over time as measured in Example 1.
Figure 5D:
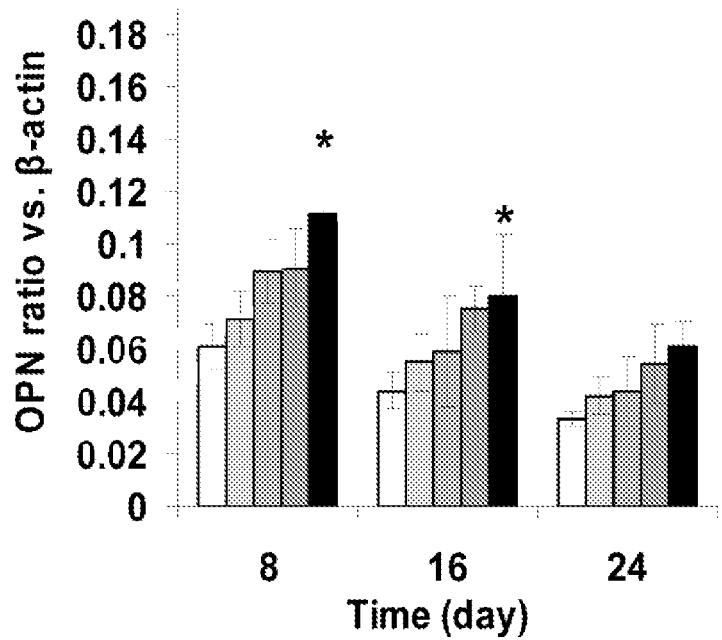
FIG. 5D shows the effect of the immobilized modular peptides on OPN expression in hMSCs over time as measured in Example 1.
Figure 5E:
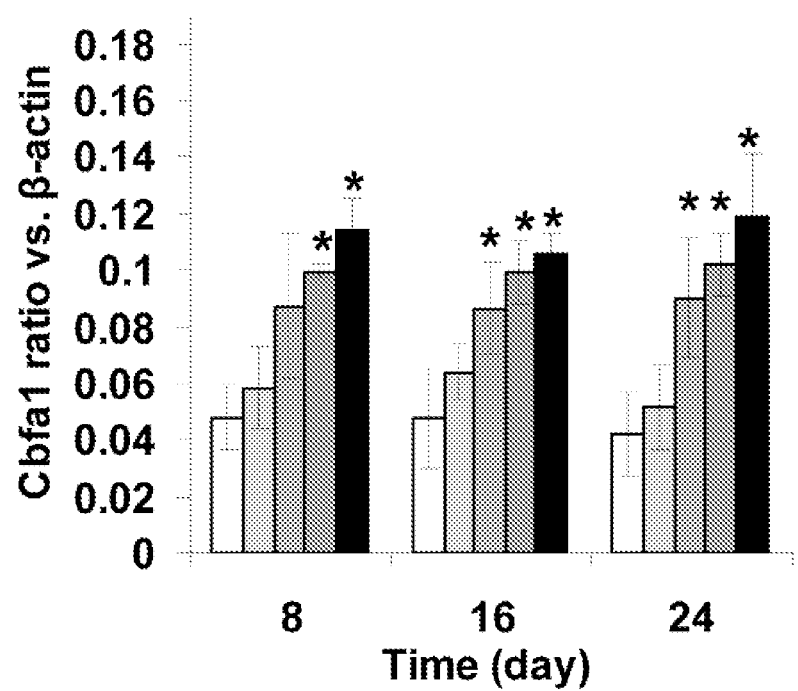
FIG. 5E shows the effect of the immobilized modular peptides on Cbfa1 expression in hMSCs over time as measured in Example 1.

Furthermore, the correlation of osteogenic differentiation to the expression levels of osteogenesis-related proteins, including OCN, osteopontin (OPN), and core-binding factor alpha 1 (Cbfa1) via RT-PCR using the primers indicated (FIG. 5A) were analyzed. OCN expression was significantly increased on HeBGa3 substrates at all time points studied when compared to TCP (p<0.01), PLG (p<0.01), and HPS (p<0.04) (FIGS. 5B and C). OPN expression was significantly increased on HeBGa3 substrates at day 8 (p=0.005) and day 16 (p=0.032) when compared to TCP (FIGS. 5B and D). Cbfa1 expression was increased on HeBGa3 substrates at all time points studied when compared to TCP (p<0.002) (FIGS. 5B and E). Expression of osteogenesis-related genes was also enhanced on HeBGu3 substrates compared to TCP, PLG, and HPS, but to a lesser extent than HeBGa3 substrates. Specifically, HeBGu3 substrates enhanced OCN expression at day 8 and enhanced Cbfa1 expression at all time points studied. Taken together, the RT-PCR analyses indicate that eBGa3-treated films promote expression of osteogenic markers to a greater extent than eBGu3-treated films, and this result is in agreement with the aforementioned analyses of ALP activity, mineralized tissue formation, BMP-2 production, and OCN production. It is noteworthy that Cbfa1 expression was also enhanced on HA-coated films when compared to TCP at day 16 (p=0.031) and day 24 (p<0.044), indicating that the HA-coated film alone slightly influences expression of pro-osteogenic transcription factors.

EXAMPLE 2

In this Example, modular peptides are synthesized and used to coat a HA-based biomaterial. The binding behavior and bioactivity of the modular peptides is then analyzed.

Specifically, modular peptides (Table 3) were synthesized and analyzed using the methods described in Example 1.

TABLE 3

Sequences of modular peptide growth factors and natural template.

| Peptide | Amino Acid Sequence |
|---|---|
| Human OCN | γEPPRγEVCγEL (AAs: 17-25) (SEQ ID NO: 20) |
| VEGF helical region | KVKFMDVYQRSYCHP (AAs: 14-28) (SEQ ID NO: 22) |
| VEGF mimic* | KLTWQELYQLKYKGI (SEQ ID NO: 23) |
| VEGF-OCN | KLTWQELYQLKYKGI-GGGAAAA-γEPRRγEVAγEL (SEQ ID NO: 18) |

*First synthesized by Pedon, et al., inspired by the VEGF helical region (AAs: 14-25), PNAS, 102(4): 14215-14220 (2005).

Figure 7A:
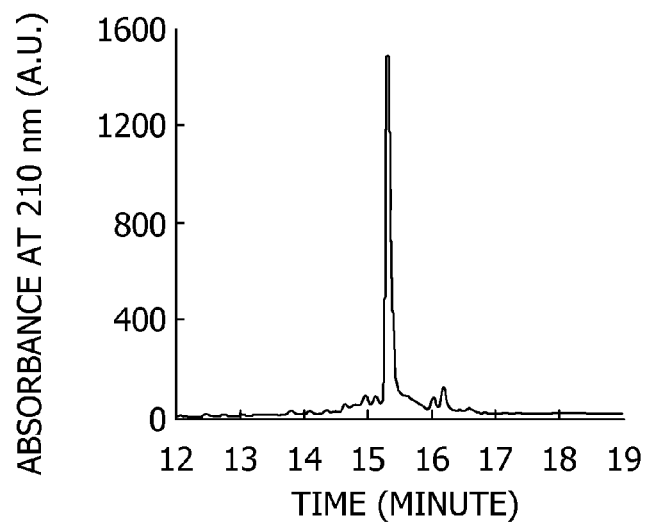
FIG. 7A shows the high performance liquid chromatography (HPLC) spectrum of modular VEGF-OCN peptide in Example 2.
Figure 7B:
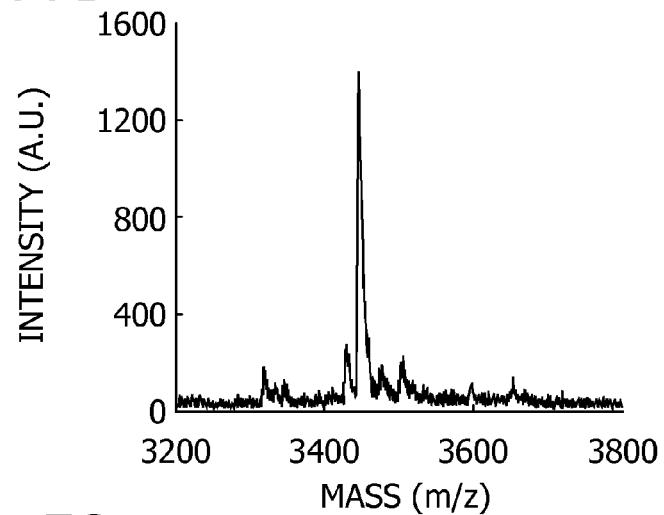
FIG. 7B shows a MALDI-TOF spectrum of modular VEGF-OCN peptide in Example 2.
Figure 7C:
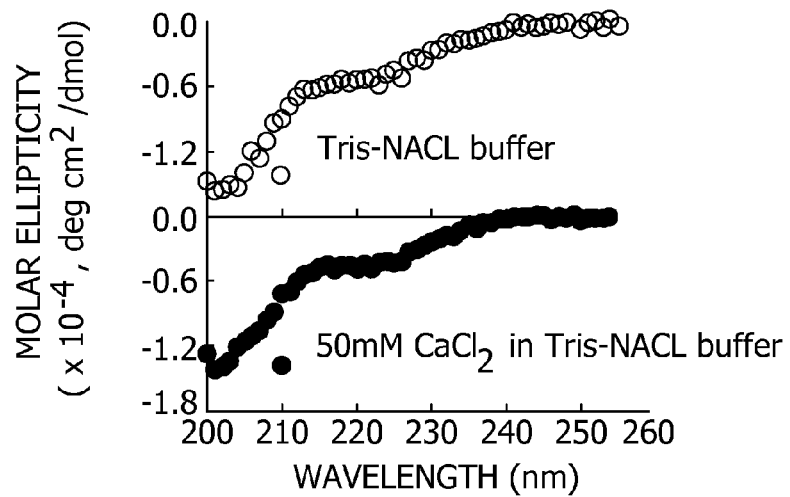
FIG. 7C shows circular dichroism (CD) spectrum of modular VEGF-OCN peptide in Example 2.

The molecular characteristics of the synthesized modular peptides are shown in FIGS. 7A-7C. The HPLC, MALDI-TOF and CD spectra confirmed that the peptide is successfully synthesized, bearing partial α-helical structure.

Figure 8A:
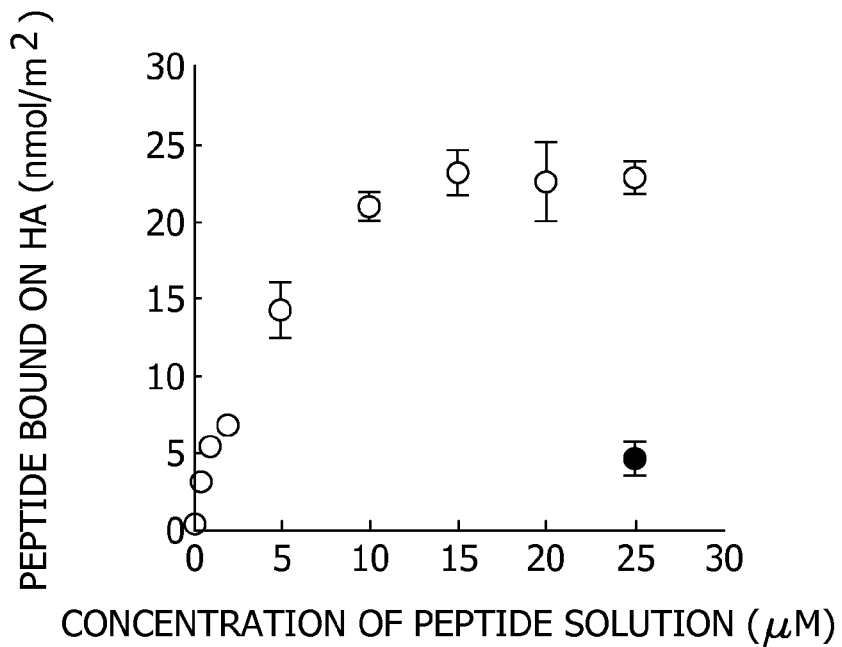
FIG. 8A shows the binding isotherm of modular VEGF-OCN peptide on HA particle as measured in Example 2. Empty symbols represent VEGF-OCN and filled symbol represents VEGF-mimic.
Figure 8B:
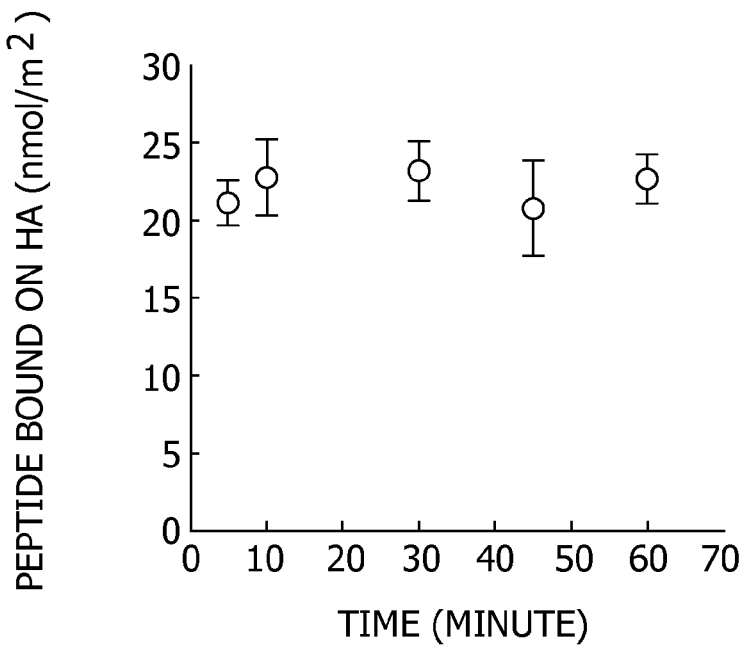
FIG. 8B shows the binding isotherm of modular VEGF-OCN peptide on HA particle over time as measured in Example 2.
Figure 8C:
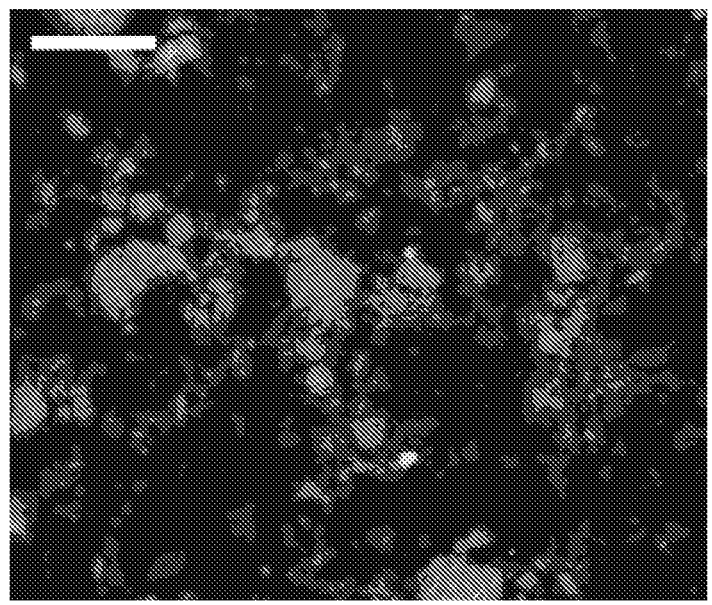
FIG. 8C shows fluorescently labeled VEGF-OCN peptide bound on HA particle.
Figure 8D:
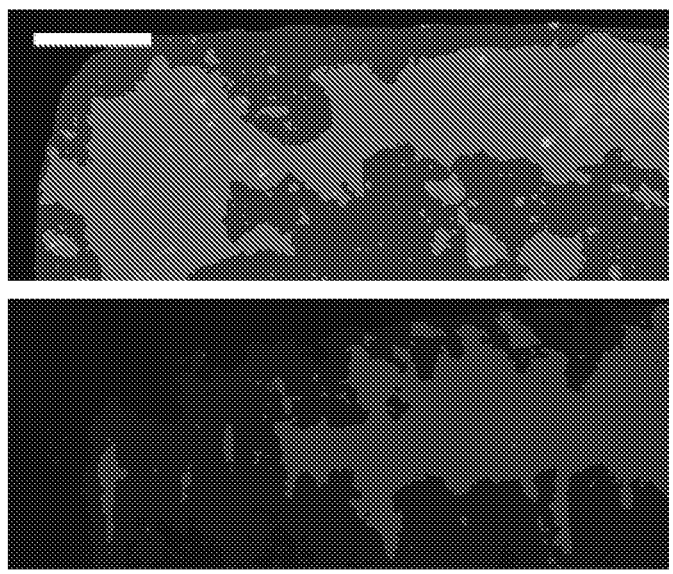
FIG. 8D shows qualitative comparison of the binding of VEGF-OCN (top) and VEGF-mimic (bottom) on HA particle.

The binding behavior of the peptides (both modular peptide, VEGF-OCN (SEQ ID NO:18), and VEGF-mimic) were analyzed and compared as described above. The amount of bound VEGF-OCN on the HA particle increased with peptide concentration and reached saturation at 15 µM (FIG. 8A). Additionally, it was found that the binding of modular peptide, VEGF-OCN (SEQ ID NO:18) to HA particle was completed within five minutes (see FIGS. 8B and 8C). The amount of VEGF-mimic to HA slab was shown to be much less than that of VEGF-OCN (see FIG. 8D).

Biological Activity of Modular Peptides

Figure 9A:
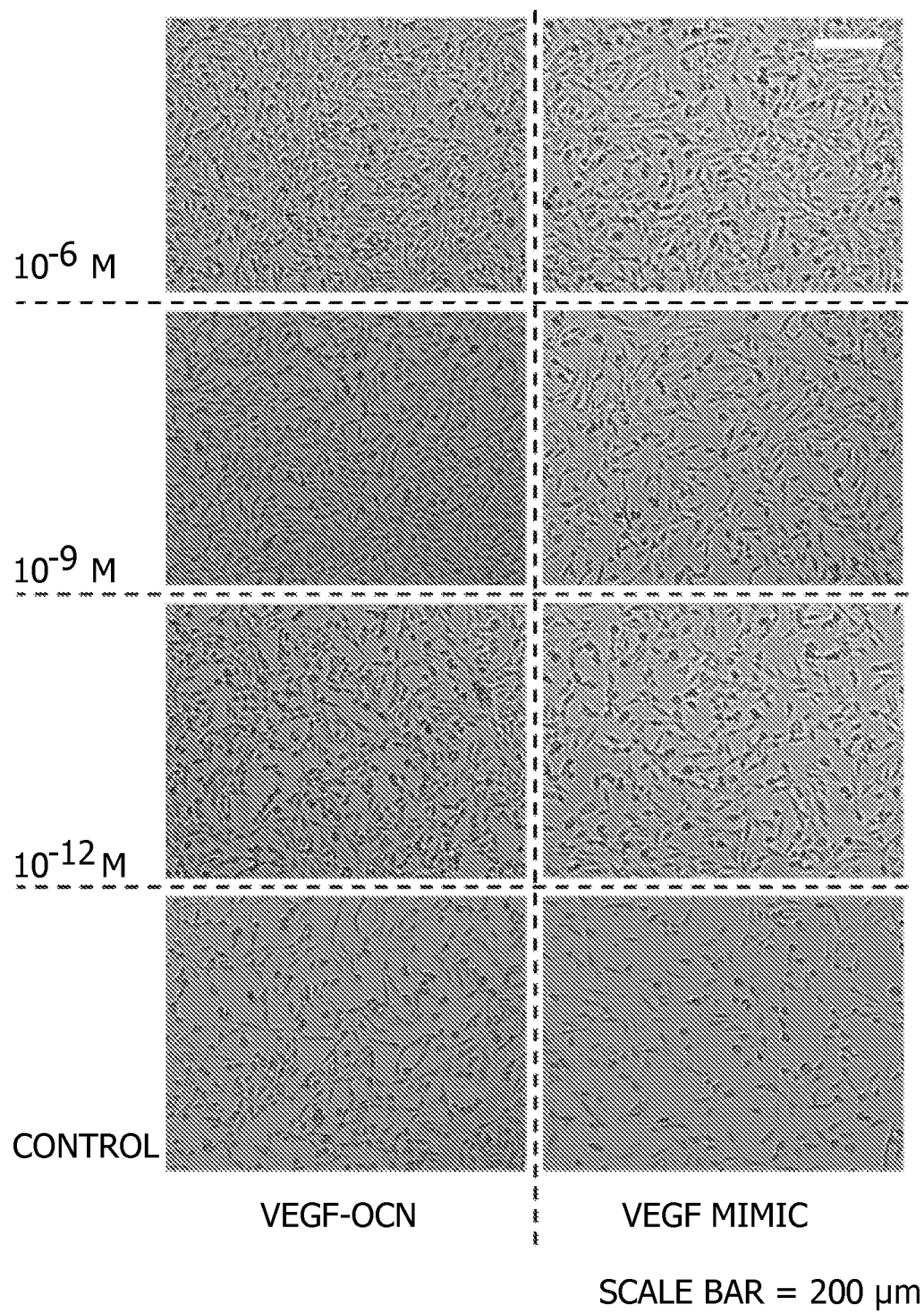
FIG. 9A shows optical micrographs showing the effect of soluble modular peptides on C166-GFP cell proliferation as determined in Example 2.
Figure 9B:
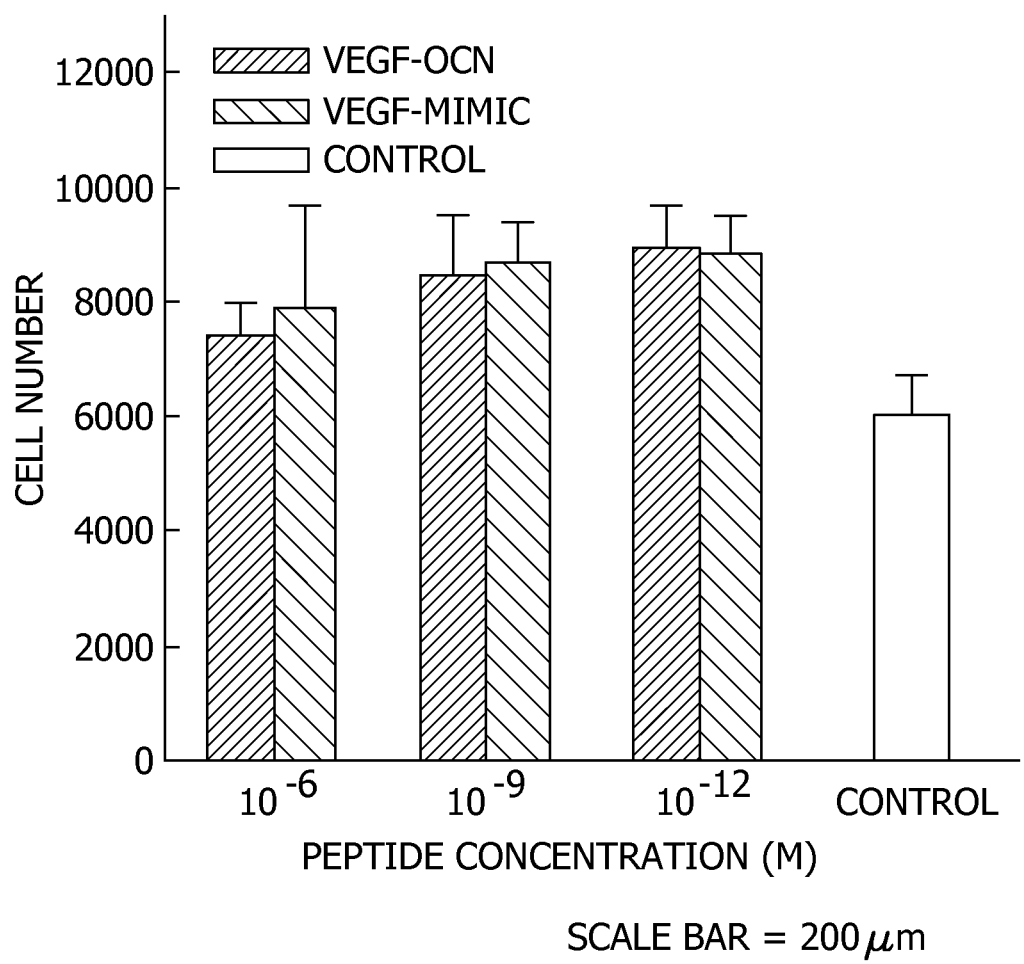
FIG. 9B shows the effect of soluble modular peptides on C166-GFP cell proliferation in Example 2.

To determine biological activity of VEGF portion for promoting cell proliferation, mouse yolk sac endothelial C166-GFP cells were seeded at a density of $3.12 \times 10^3$ cells/cm$^2$ ($1 \times 10^3$ cells per well) in 96-well plate, allowed to attach for six hours, and then stimulated with either VEGF-OCN or VEGF-mimic After 48 hours of stimulation, optical micrographs were taken using Olympus IX-51 microscope and cell numbers were determined by CYQUANT assay. Results are shown in FIGS. 9A and 9B. Specifically, the results showed that the addition of VEGF-OCN or VEGF-mimic resulted in an increase in cell number to the similar extent when compared to a control, which indicated that the presence of HA-binding portion in VEGF-OCN does not deteriorate the characteristic of VEGF-mimic portion.

Figure 10A:
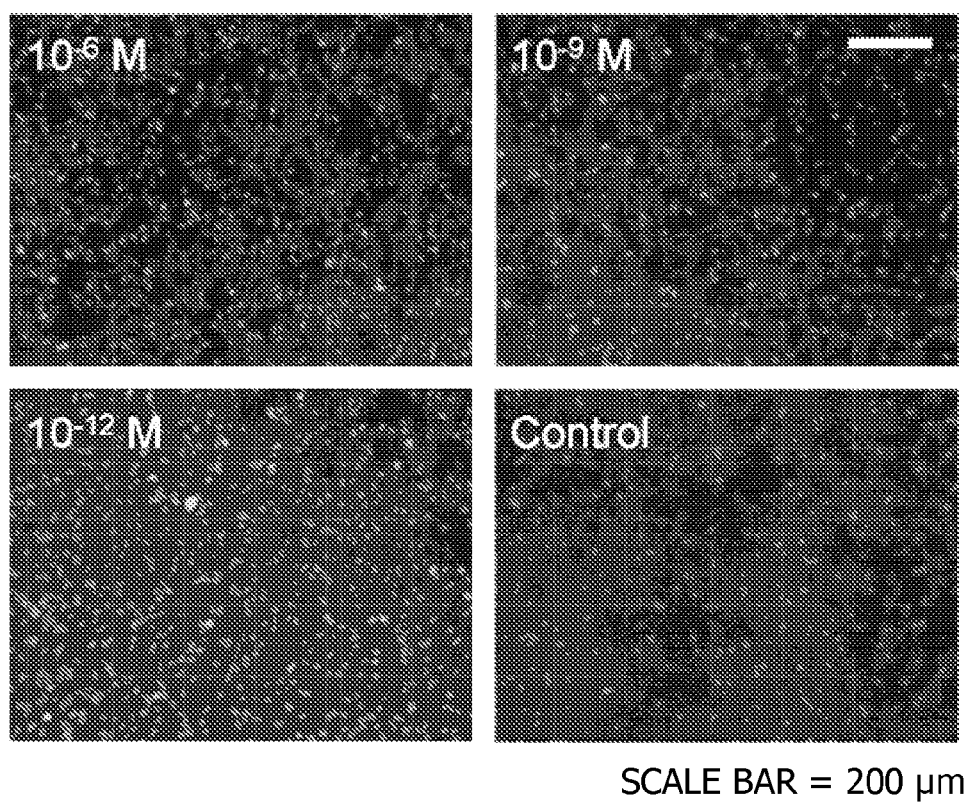
FIG. 10A shows fluorescence micrographs of C166-GFP cells cultured on VEGF-OCN or VEGF-mimic immobilized on HA slab in Example 2.

Cells were again seeded at a density of $2 \times 10^4$ cells/cm$^2$ ($4 \times 10^4$ cells per well) in 24-well plate. Prior to seeding, HA slabs (1 cm×1 cm) were incubated in peptide solution (PBS) for four hours at 37° C. and copiously rinsed with deionized water, and then placed in a well of the 24-well plate. After 1-day culture, cells were treated with 2 µM calcein AM solution, and imaged using Olympus IX-51 microscope. The fluorescence micrographs of C166-GFP cells cultured in the presence of VEGF-OCN or VEGF mimic are shown in FIG. 10A.

Figure 10B:
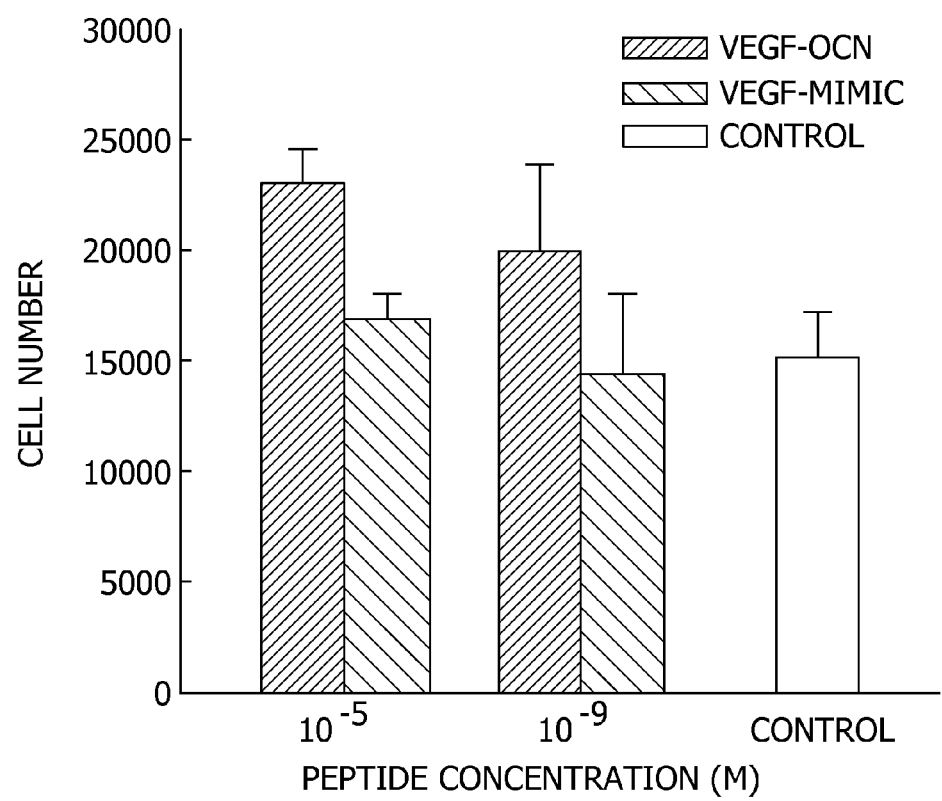
FIG. 10B shows the effect of immobilized modular peptides on C166-GFP cell proliferation in Example 2.
Figure 11A:
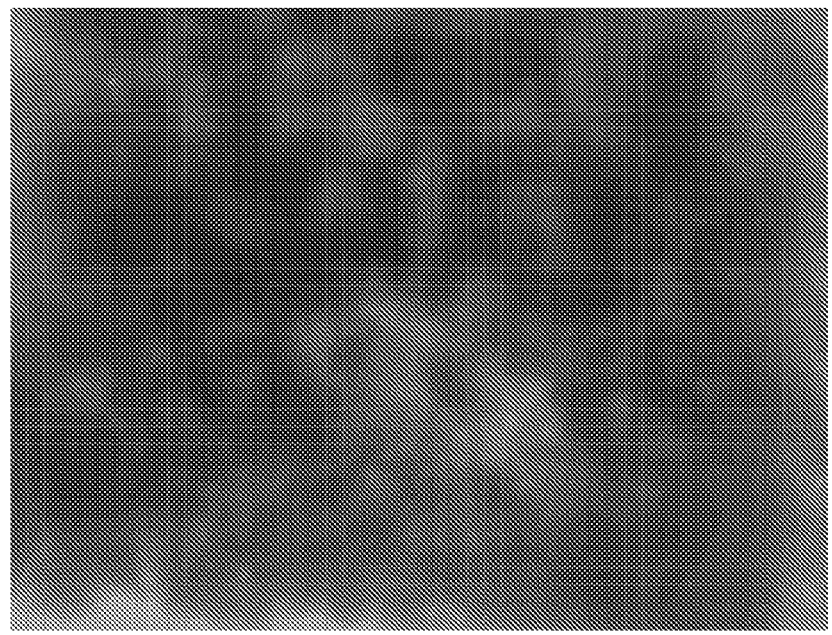
FIG. 11A shows a fluorescence micrograph of eBGa3 peptides that are incorporated on a HA slab using dip coating.
Figure 11B:
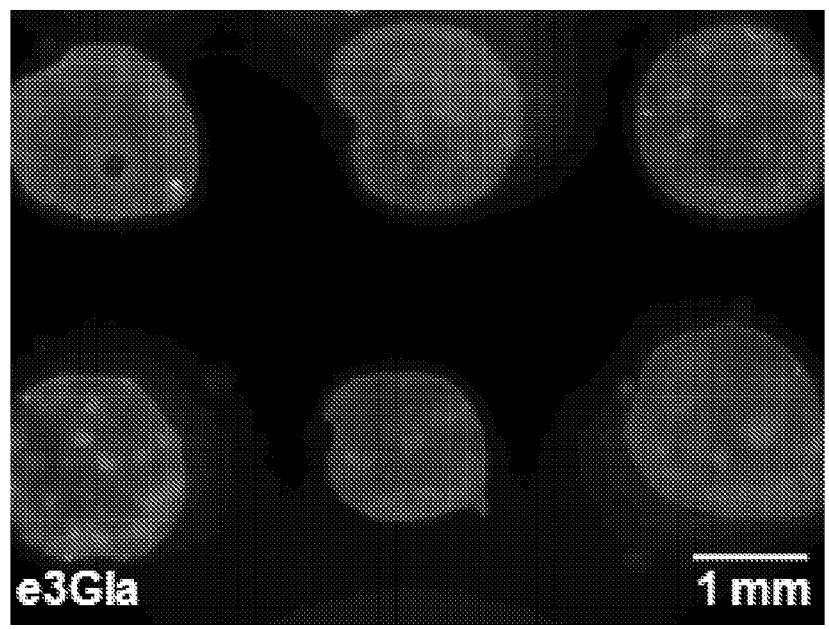
FIG. 11B shows a fluorescence micrograph of eBGa3 peptides that are incorporated on a HA slab using stamping.
Figure 11C:
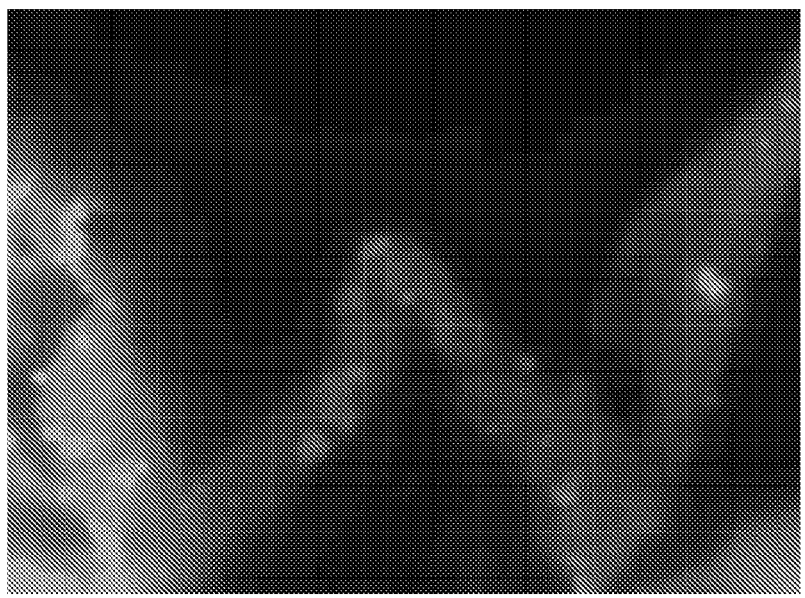
FIG. 11C shows a fluorescence micrograph of eBGa3 peptides that are incorporated on a HA slab using a painting method.
Figure 11D:
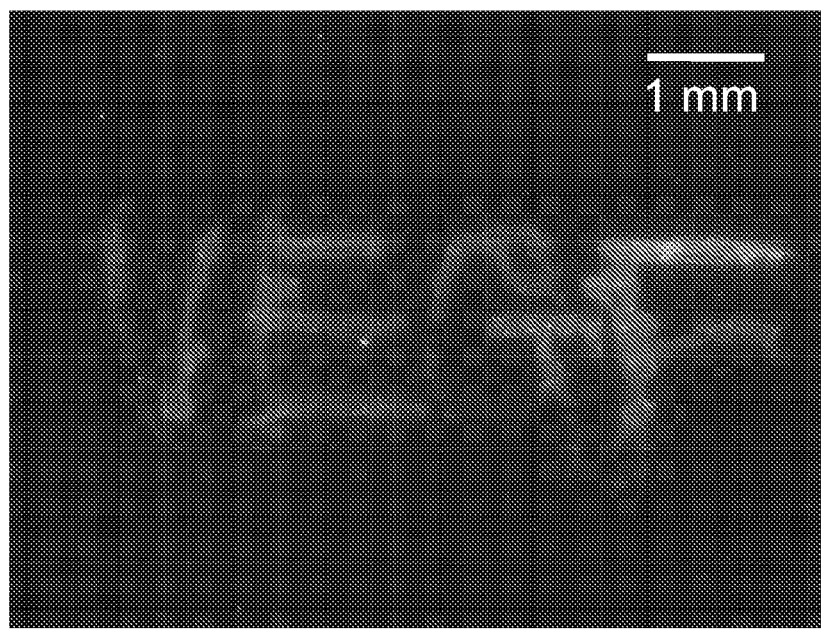
FIG. 11D shows a fluorescence micrograph of VEGF-OCN peptides that are incorporated on a HA slab using a painting method.
Figure 11E:
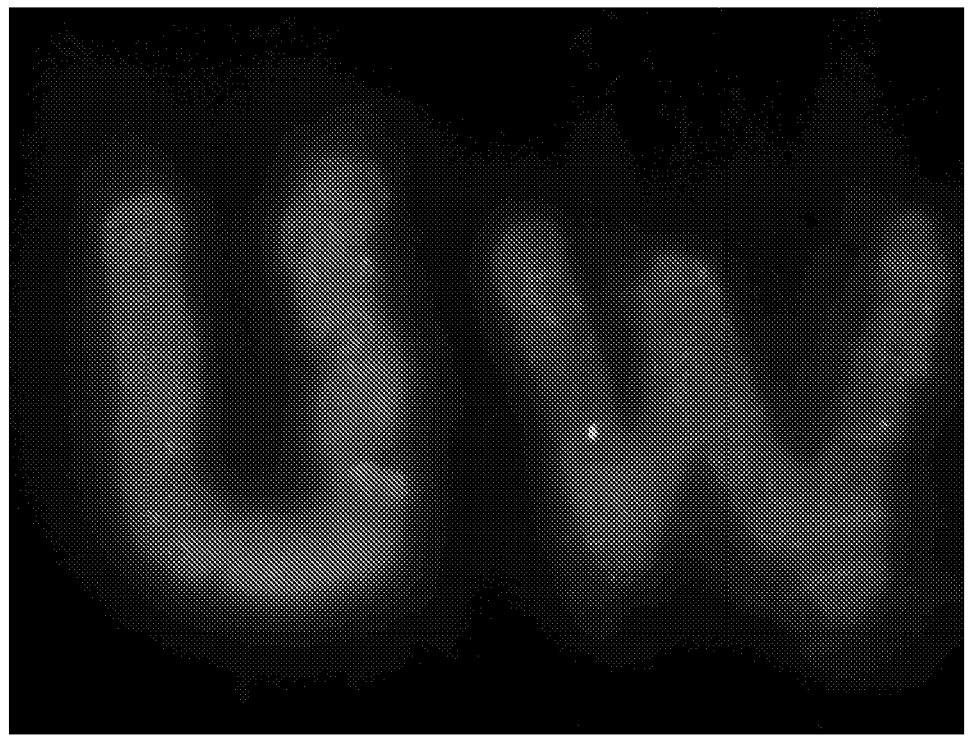
FIG. 11E shows a fluorescence micrograph of VEGF-OCN peptides that are incorporated on a HA slab using a painting method.

Additionally, a cell number count of the C166-GFP cells as cultured in the presence of VEGF-OCN or VEGF mimic was determined For the cell count, cells were seeded at a density of $5 \times 10^3$ cells/cm$^2$ ($1 \times 10^4$ cells per well) in a 24-well plate. After 2-day culture, cells were detached from the HA slab and cell number was assessed using CYQUANT assay. As shown in FIG. 10B, there was a significant difference in the increase in the cell number between VEGF-OCN treated and VEGF-mimic treated slabs. This indicated that the VEGF-OCN could bind to the HA slab and promoted cell proliferation. Cell number found on VEGF-mimic treated slab was similar to that of the control, suggesting that VEGF-mimic did not bind to the HA slab, resulting in no stimulation on VEGF-mimic treated HA slab.

What is claimed is:

1. A modular peptide for non-covalently binding to a surface of a biomaterial, the modular peptide comprising: a hydroxyapatite-binding portion, a spacer portion, and a biomolecule-derived portion, wherein the hydroxyapatite-binding portion comprises an amino acid sequence selected from the group consisting of SEQ ID NO:1, SEQ ID NO:2, SEQ ID NO:3, SEQ ID NO:4, SEQ ID NO:5, and SEQ ID NO:6.

2. The modular peptide as set forth in claim 1 wherein the biomaterial is selected from the group consisting of hydoxyapatite and hydroxyapatite-based materials.

3. The modular peptide as set forth in claim 1 wherein the spacer portion is an amino acid sequence capable of forming an α-helix.

4. The modular peptide as set forth in claim 1 wherein the spacer portion is SEQ ID NO:7.

5. The modular peptide as set forth in claim 1 wherein the biomolecule-derived portion is a growth factor capable of initiating at least one of osteogenesis, angiogenesis, and osteogenic differentiation.

6. The modular peptide as set forth in claim 5 wherein the growth factor comprises an amino acid sequence selected from the group consisting of SEQ ID NO:8, SEQ ID NO:9, SEQ ID NO:10, and SEQ ID NO:11.

7. The modular peptide as set forth in claim 1 having the sequence selected from the group consisting of SEQ ID NO:12, SEQ ID NO:13, SEQ ID NO: 14, SEQ ID NO:15, SEQ ID NO:16, SEQ ID NO:17, and SEQ ID NO:18.

* * * * *